(12) United States Patent
Lin et al.

(10) Patent No.: US 7,566,780 B2
(45) Date of Patent: Jul. 28, 2009

(54) PHOSPHORUS-BASED OXAZINE COMPOUNDS AND PREPARATION METHOD OF THE SAME

(75) Inventors: Ching-Hsuan Lin, Taichung (TW); Ya-Ru Taso, Taipei (TW); Chau-Wei Hsieh, Changhua County (TW); Hao-Hsin Lee, Taichung (TW); Fang-Hsien Su, Taipei (TW); An-Pang Tu, Taipei (TW); Kuen-Yuan Hwang, Taipei (TW)

(73) Assignees: Chang Chun Plastics Co., Ltd., Hsinchu County (TW); National Chung Hsing University, Taichung (TW)

( * ) Notice: Subject to any disclaimer, the term of this patent is extended or adjusted under 35 U.S.C. 154(b) by 0 days.

(21) Appl. No.: 12/017,067

(22) Filed: Jan. 21, 2008

(65) Prior Publication Data

US 2009/0171120 A1  Jul. 2, 2009

(30) Foreign Application Priority Data

Dec. 28, 2007  (TW) .............................. 96151045 A

(51) Int. Cl.
*C07D 413/02* (2006.01)
*C07D 413/14* (2006.01)

(52) U.S. Cl. ......................................... 544/90; 544/92

(58) Field of Classification Search .................. 544/90, 544/92

See application file for complete search history.

(56) References Cited

U.S. PATENT DOCUMENTS

| 6,005,064 | A | 12/1999 | Hirai et al. |
| 6,900,269 | B2 | 5/2005 | Hwang et al. |
| 7,041,772 | B2 | 5/2006 | Aizawa et al. |
| 7,053,138 | B2 * | 5/2006 | Magendie et al. ............ 523/451 |

OTHER PUBLICATIONS

Seong-Woo Choi et al., "Synthesis Characterization and Thermal Degradation of Functional Benzoxazine Monomers and Polymers Containing Phenylphosphine Oxide", Polymer Degradation and Stability 91 (2006) 1166-1178.

Ching Hsuan Lin et al., "Synthesis and Properties of Flame-Retardant Benzoxazine by Three Approaches", Journal of Polymer Science: Part A: Polymer Chemistry DOI 10. 1002/Pola, p. 3454-3468.

\* cited by examiner

*Primary Examiner*—Kahsay T Habte
(74) *Attorney, Agent, or Firm*—Jianq Chyun IP Office

(57) ABSTRACT

The present invention provides phosphorus-based oxazine compounds and the preparation method thereof. The phosphorus-based oxazine compounds of the present invention can provide better fire-resistant characteristics, while the preparation method for the phosphorus-based oxazine compound of the present invention can offer high yields and/or high purity phosphorus-based oxazine compounds.

8 Claims, 20 Drawing Sheets

PHOSPHORUS-BASED OXAZINE COMPOUNDS AND PREPARATION METHOD OF THE SAME

CROSS-REFERENCE TO RELATED APPLICATION

This application claims the priority benefit of Taiwan application serial no. 96151045, filed on Dec. 28, 2007. The entirety the above-mentioned patent application is hereby incorporated by reference herein and made a part of specification.

BACKGROUND OF THE INVENTION

1. Field of Invention

The present invention relates to a benzoxazine compound and a preparation method for the benzoxazine compound. More particularly, the present invention relates to a phosphorus-based oxazine compound and a preparation method of the phosphorus-based oxazine compound.

2. Description of Related Art

Although the latest developed benzoxazine resin may be classified as one kind of phenolic resin, it actually is quite different from the conventional phenolic resin. The benzoxazine resin affords high glass transition temperature (Tg), high modulus, low moist absorption rate, excellent electrical characteristics, and high charyield. Moreover, there are more advantages for the benzoxazine resins, including no need for highly acidic catalysts and no byproducts during curing, the ring-opening curing after heating the monomer, and almost no voluminal variations after curing.

So far, the most commonly used benzoxazine compounds can be categorized as B-m type and B-a type compounds. The B-m type compounds are synthesized from bisphenol A, formaldehyde and methylamines, while the B-a type compounds are synthesized from bisphenol A, formaldehyde and aniline. The preparation methods for synthesizing the B-m type and the B-a type compounds are shown as follows:

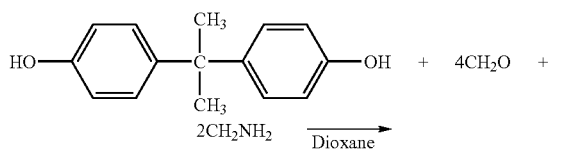

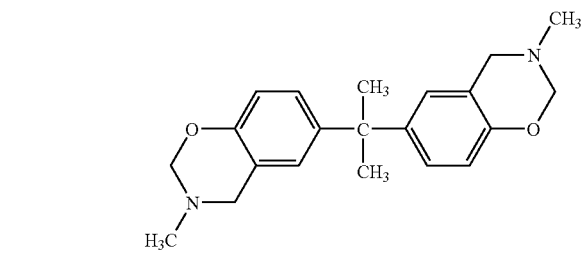

B-m

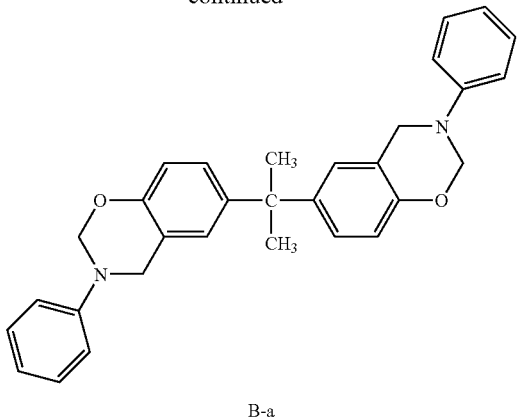

B-a

Based on the published papers, the benzoxazine compounds were synthesized from bisphenol A, formaldehyde and amines with mono-functional groups. If the benzoxazine compounds were synthesized from the amines with bi-functional groups, formaldehyde and phenols with mono-functional groups, large insoluble molecules of high molecular weights would form. It is because the functional group —$NCH_2OH$ would have condensation reaction with the amino group of aniline, and —$NCH_2OH$ would have dehydration reaction with the para- or ortho-hydrogen of aniline to form high molecular weight insolubles. Due to the formation of high molecular weight insolubles, the synthesized benzoxazine compounds come up with inferior purity and low yield rates.

Moreover, the fire-resistant characteristics of the benzoxazine resins, though superior to those of the conventional phenolic resins, can be further improved for extensive applications.

SUMMARY OF THE INVENTION

The present invention provides a phosphorus-based oxazine compound with better fire-resistant characteristics.

The present invention provides a preparation method of a phosphorus-based oxazine compound by decreasing the formation of insoluble materials during the process.

The present invention provides a preparation method for a phosphorus-based oxazine compound, which is able to prepare the phosphorus-based oxazine compound of high purity.

The present invention provides a preparation method of a phosphorus-based oxazine compound with high yields.

The present invention provides a phosphorus-based oxazine compound with the structure shown in chemical formula (I):

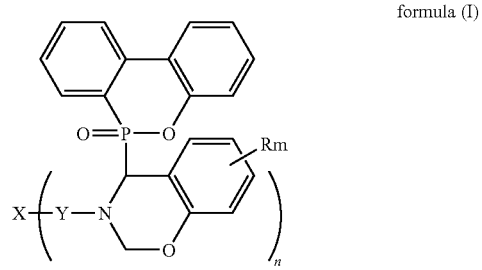

formula (I)

wherein n represents 1 or 2. when n is 1, X represents a hydrogen, a $C_1$-$C_6$ alkyl group, a $C_1$-$C_6$ alkyl group, a $C_1$-$C_6$ alkoxyl group, $CF_3$, $OCF_3$, a phenyl group, a halogen group, a phenoxy group or a $C_3$-$C_7$ cyclic alkyl group. When n is 2, X represents a single bond or

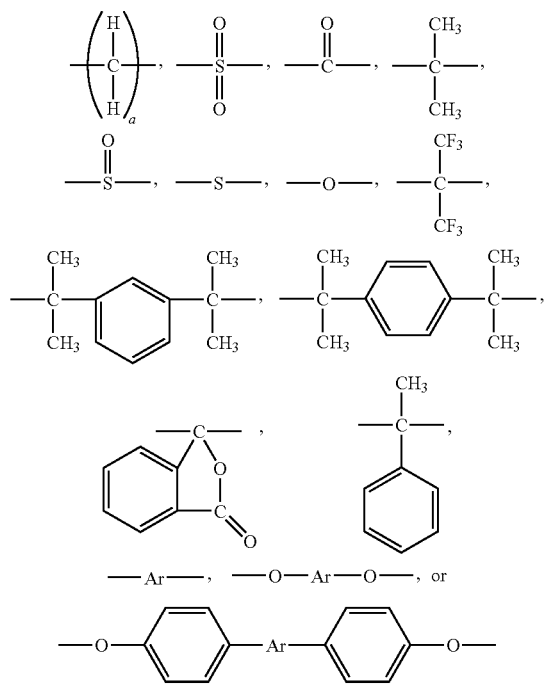

wherein a is an integer ranging from 1 to 16, Ar represents

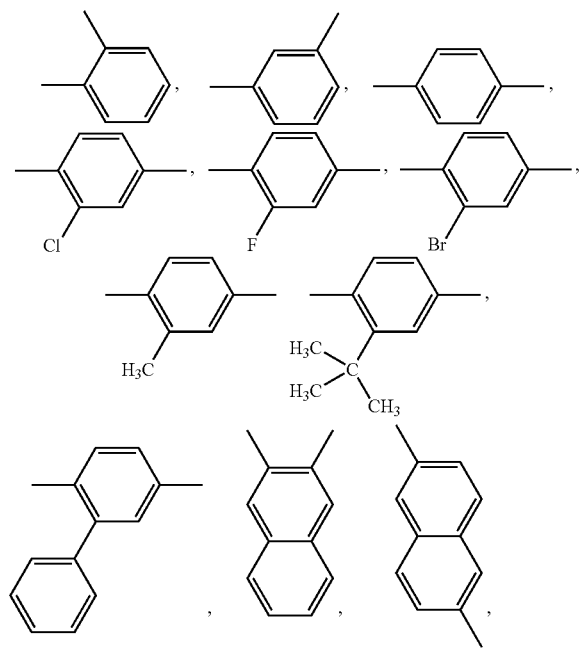

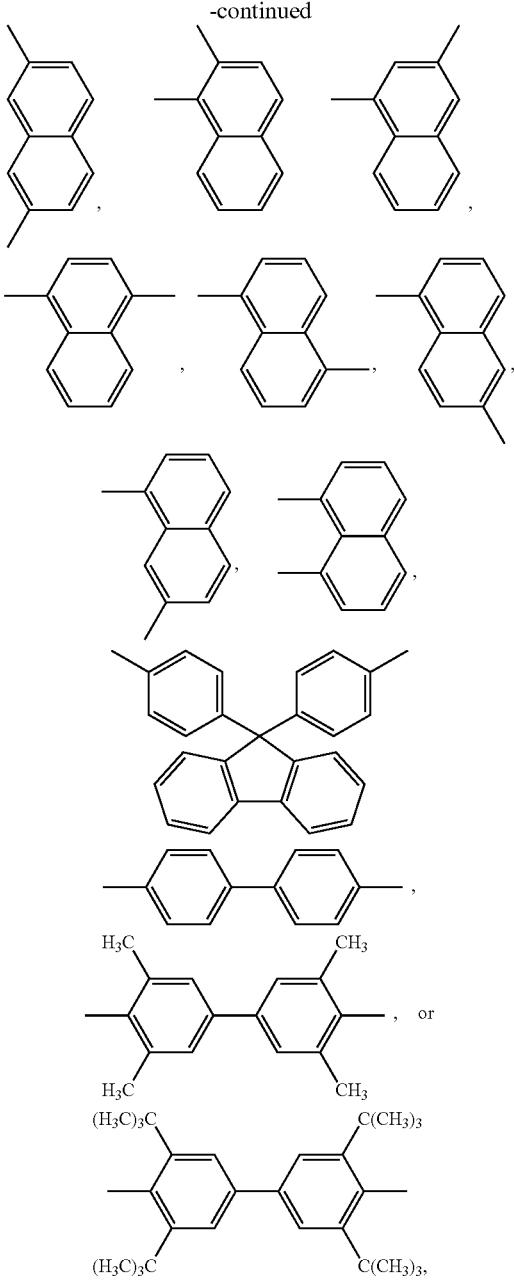

Y represents

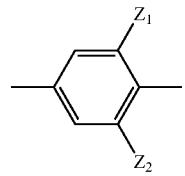

or a single bond, wherein $Z_1$ or $Z_2$ individually represents a hydrogen, a $C_1$-$C_6$ alkyl group, a $C_1$-$C_6$ alkoxyl group, $CF_3$, a phenyl group, a halogen group, a phenoxy group or a $C_3$-$C_7$ cyclic alkyl group, m represents 1 or 2, R represents a hydrogen, a $C_1$-$C_6$ alkyl group, a $C_1$-$C_6$ alkoxyl group, $CF_3$, $OCF_3$, a phenyl group, a halogen group, a phenoxy group or a $C_3$-$C_7$ cyclic alkyl group, and when m is 2, R represents the same or different groups.

According to the embodiment of this invention, for the above phosphorus-based oxazine compound, when n is 2, X is the center of symmetry.

The present invention provides a preparation method of a phosphorus-based oxazine compound. The phosphorus-based oxazine compound has a structure as shown in chemical formula (II):

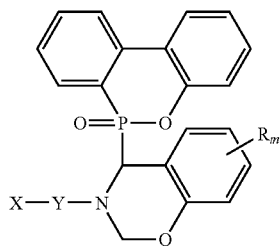

formula (II)

wherein X represents a hydrogen, a $C_1$-$C_6$ alkyl group, a $C_1$-$C_6$ alkyl group, a $C_1$-$C_6$ alkoxyl group, $CF_3$, $OCF_3$, a phenyl group, a halogen group, a phenoxy group or a $C_3$-$C_7$ cyclic alkyl group. Y represents

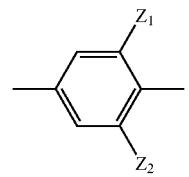

or a single bond, wherein $Z_1$ or $Z_2$ individually represents a hydrogen, a $C_1$-$C_6$ alkyl group, a $C_1$-$C_6$ alkoxyl group, $CF_3$, a phenyl group, a halogen group, a phenoxy group or a $C_3$-$C_7$ cyclic alkyl group, m represents 1 or 2, R represents a hydrogen, a $C_1$-$C_6$ alkyl group, a $C_1$-$C_6$ alkoxyl group, $CF_3$, $OCF_3$, a phenyl group, a halogen group, a phenoxy group or a $C_3$-$C_7$ cyclic alkyl group, and when m is 2, R represents the same or different groups. The preparation method of the phosphorus-based oxazine compound comprises: mixing the following compounds

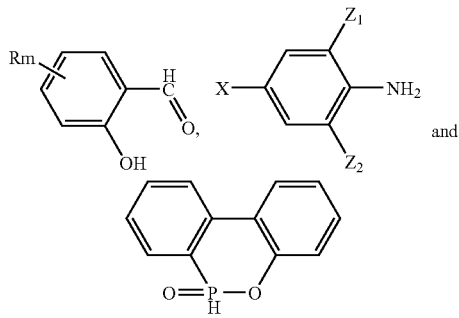

to form the compound of the following formula (III):

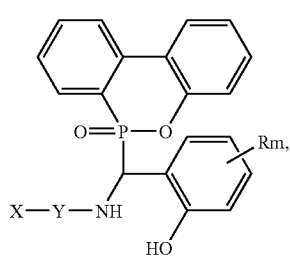

formula (III)

wherein X, Y, R and m are defined as described in the above formula (II), subsequently formaldehyde or trioxymethylene is added to obtain the final product.

According to the embodiment of this invention, for the preparation method of the phosphorus-based oxazine compound, the compound of formula (III) is formed in a single step by simultaneously contacting and mixing the following compounds

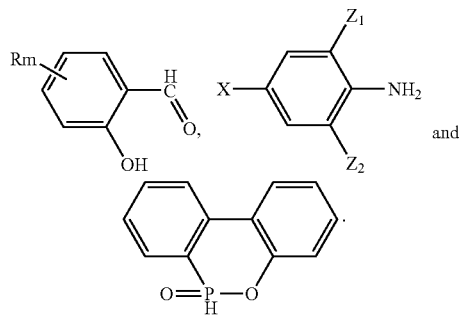

According to the embodiment of this invention, for the preparation method of the phosphorus-based oxazine compound, the compound of formula (III) is formed in two-stage by first contacting and mixing

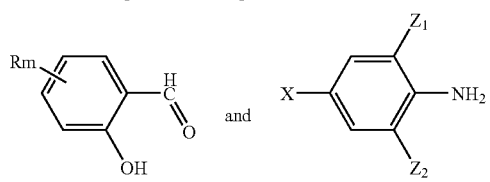

to form the compound of the following formula (IV):

formula (IV)

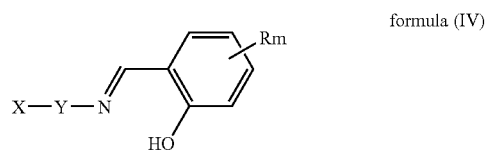

and followed by adding the compound

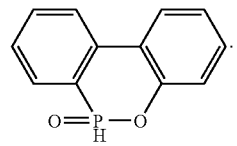

The present invention provides a preparation method of a phosphorus-based oxazine compound, the phosphorus-based oxazine compound has a structure as shown in the following formula (V):

formula (V)

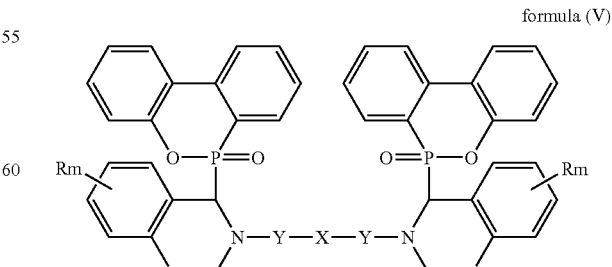

wherein X represents a single bond or

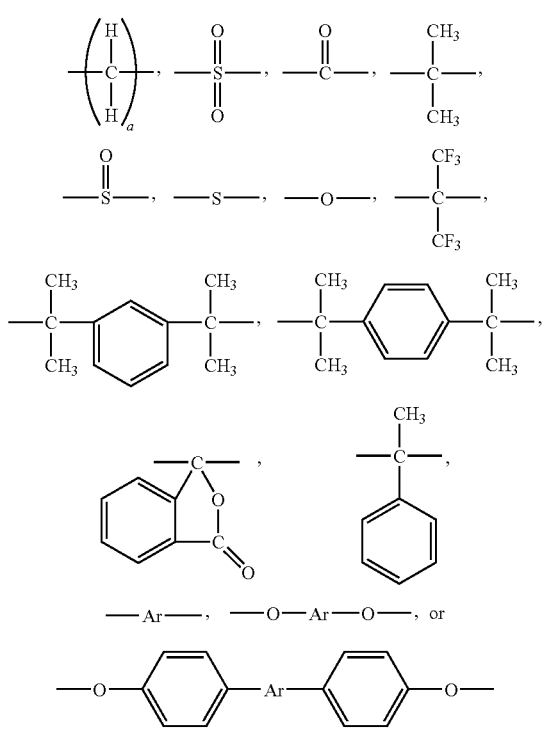

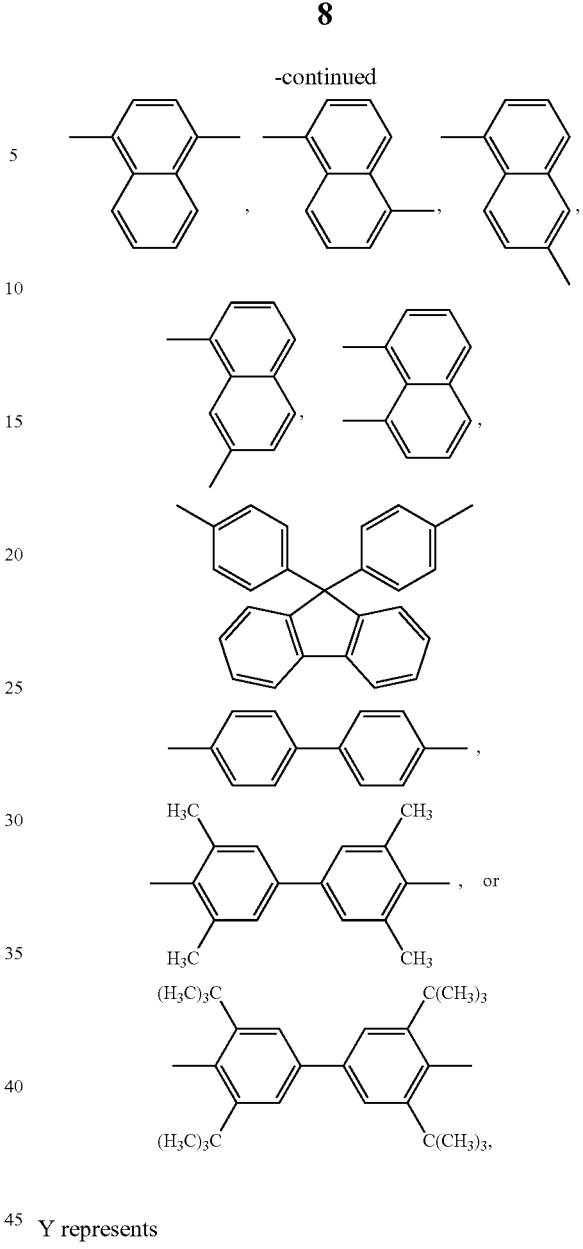

wherein a is an integer ranging from 1 to 16. Ar represents

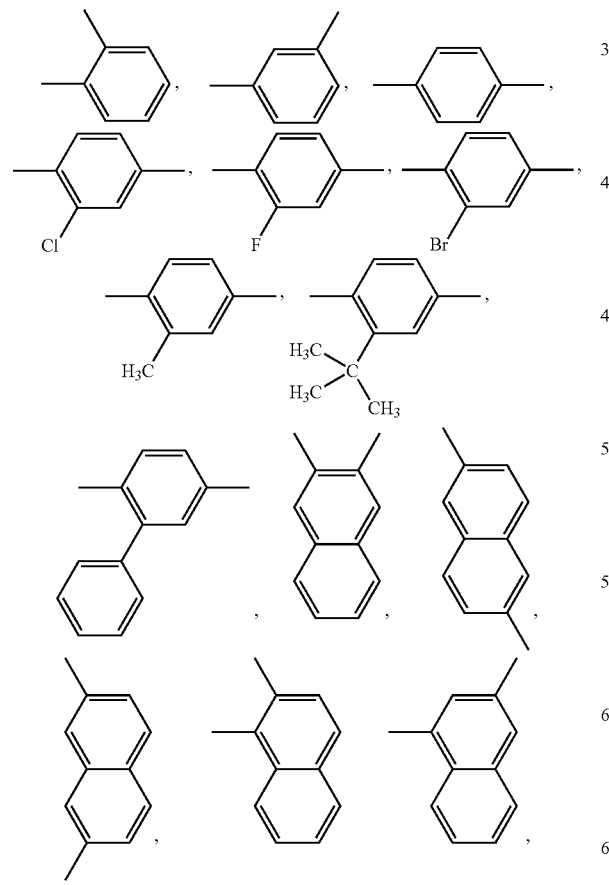

Y represents

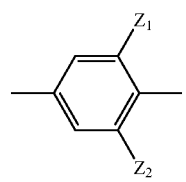

or a single bond, wherein $Z_1$ or $Z_2$ individually represents a hydrogen, a $C_1$-$C_6$ alkyl group, a $C_1$-$C_6$ alkoxyl group, $CF_3$, a phenyl group, a halogen group, a phenoxy group or a $C_3$-$C_7$ cyclic alkyl group, m represents 1 or 2, R represents a hydrogen, a $C_1$-$C_6$ alkyl group, a $C_1$-$C_6$ alkoxyl group, $CF_3$, $OCF_3$, a phenyl group, a halogen group, a phenoxy group or a $C_3$-$C_7$ cyclic alkyl group, and when m is 2, R represents the same or different groups. The preparation method of the phosphorus-based oxazine compound comprises: mixing the following compounds

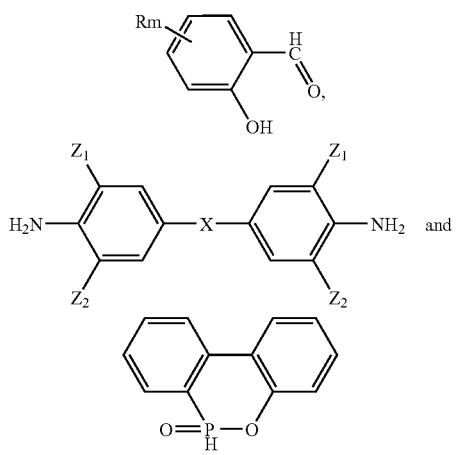

to form the following formula (VI):

formula (VI)

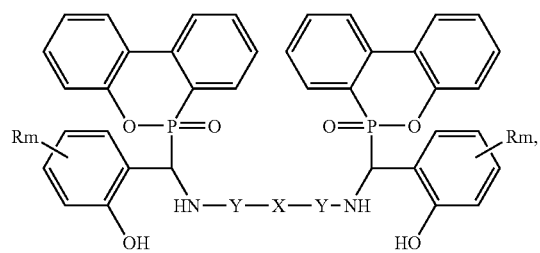

wherein X, Y, R and m are defined as described in the above formula (V), subsequently formaldehyde or trioxymethylene is added to obtain the final product.

According to the embodiment of this invention, for the preparation method of the phosphorus-based oxazine compound, the compound of formula (VI) is formed in a single step by simultaneously contacting and mixing the following compounds

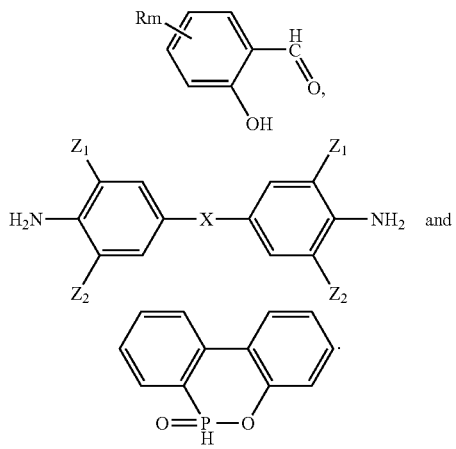

According to the embodiment of this invention, for the preparation method of the phosphorus-based oxazine compound, the compound of formula (VI) is formed in two-stage by first contacting and mixing the following compounds

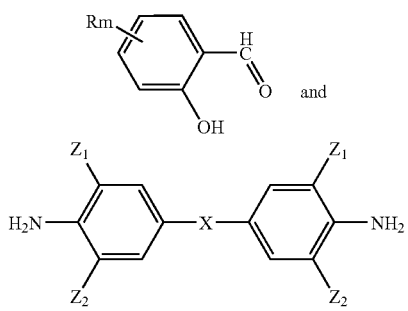 and to form the compound of the following formula (VII):

formula (VII)

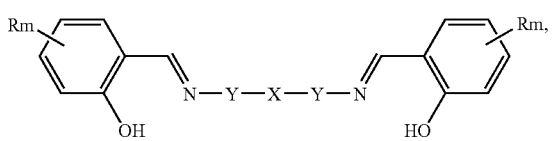

wherein X, Y, R and m are defined as described in the above formula (V), and followed by adding the compound

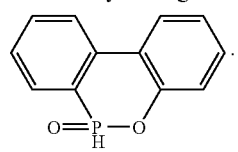

According to the embodiments of this invention, the phosphorus-based oxazine compound can provide better fire-resistant characteristics.

According to the embodiment of this invention, the preparation method of the phosphorus-based oxazine compound can afford high yields and/or high purity phosphorus-based oxazine compounds.

In order to make the aforementioned and other objectives, features and advantages of the present invention comprehensible, preferred embodiments accompanied with figures are described in detail below.

DESCRIPTION OF EMBODIMENTS

Figure 1A:
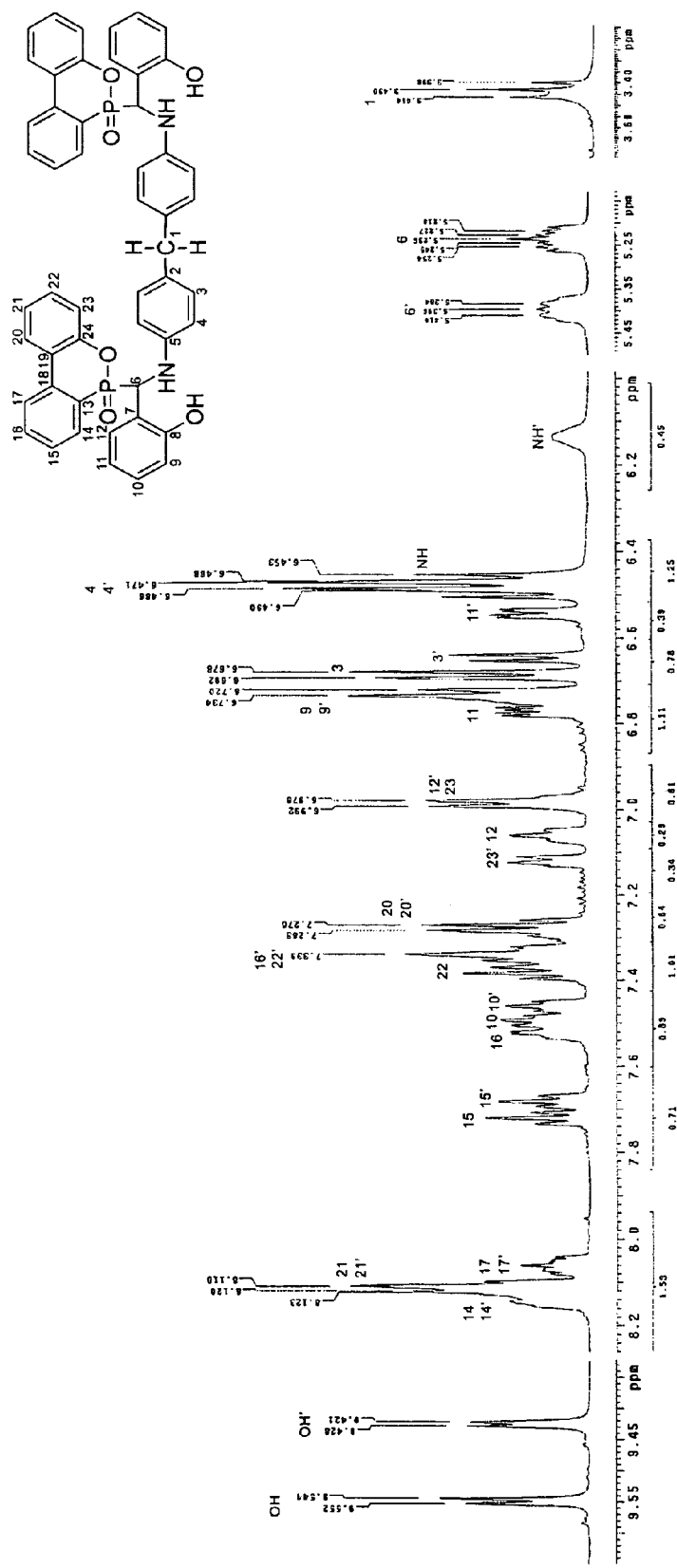
FIG. 1A and FIG. 1B are respectively 1H-NMR and 13C-NMR spectrums of the intermediate compound P-DDM-HB according to the example 2 of this invention.

The phosphorus-based oxazine compound of this invention has the structure shown as the following formula (I):

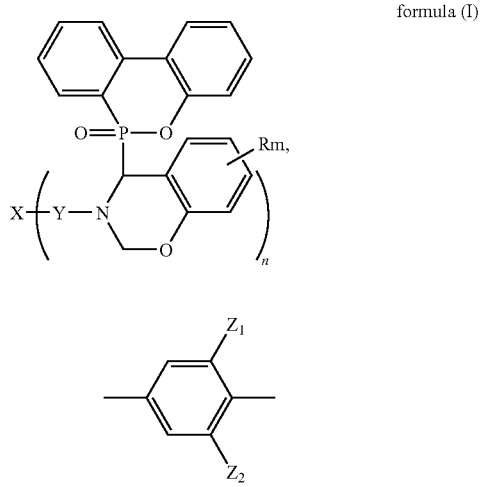

formula (I)

wherein Y represents or a single bond, wherein $Z_1$ or $Z_2$ individually represents a hydrogen, a $C_1$-$C_6$ alkyl group, a $C_1$-$C_6$ alkoxyl group, $CF_3$, a phenyl group, a halogen group, a phenoxy group or a $C_3$-$C_7$ cyclic alkyl group, m represents 1 or 2, R represents a hydrogen, a $C_1$-$C_6$ alkyl group, a $C_1$-$C_6$ alkoxyl group, $CF_3$, $OCF_3$, a phenyl group, a halogen group, a phenoxy group or a $C_3$-$C_7$ cyclic alkyl group, and when m is 2, R represents the same or different groups.

In formula (I), n represents 1 or 2. When n is 1, X represents a hydrogen, a $C_1$-$C_6$ alkyl group, a $C_1$-$C_6$ alkoxyl group, $CF_3$, $OCF_3$, a phenyl group, a halogen group, a phenoxy group or a $C_3$-$C_7$ cyclic alkyl group. When n is 2, X is a center of symmetry, such as a single bond or

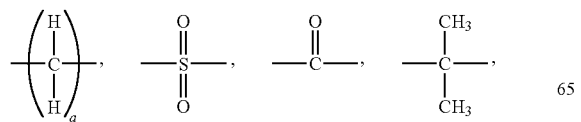

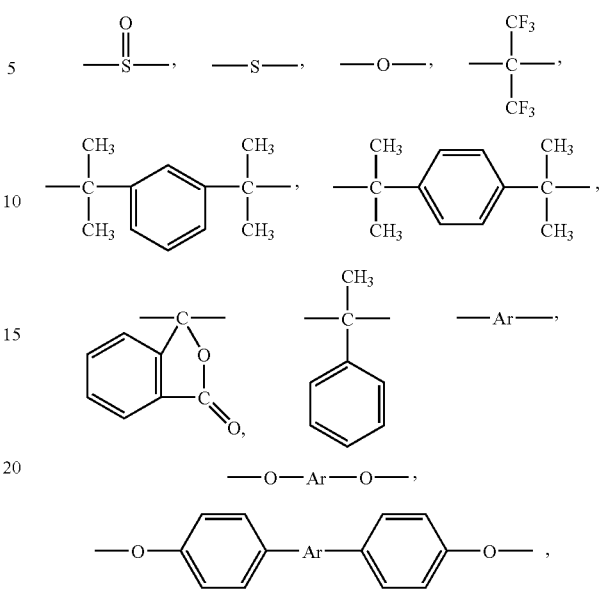

wherein a is an integer ranging from 1 to 16, Ar represents

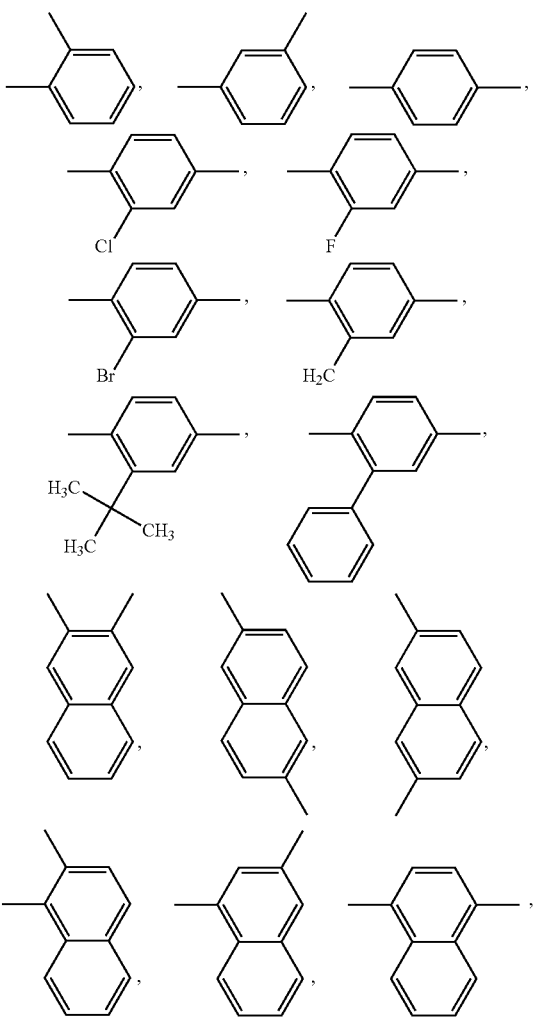

-continued

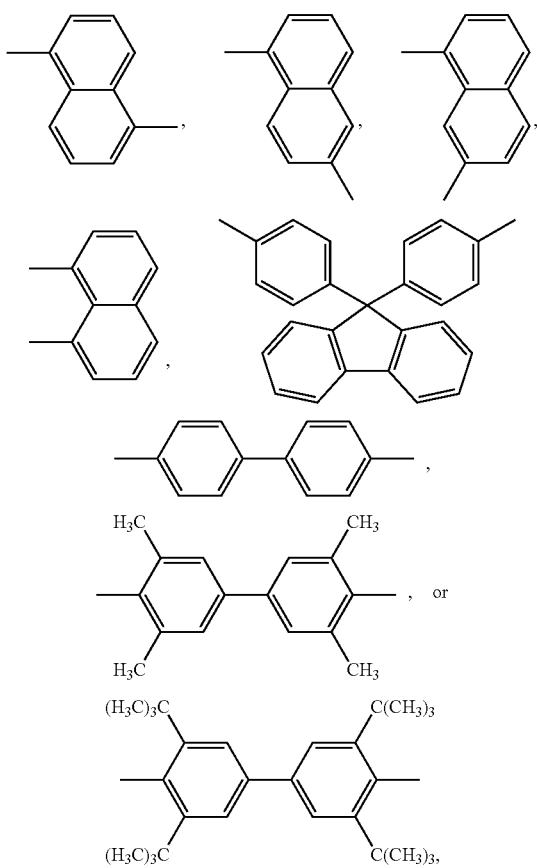

The preparation method of the phosphorus-based oxazine compound of formula (I) comprises: contacting and mixing 2-hydroxybenzaldehyde (2-HB), an amine and 10-dihydro-9-oxa-10-phosphaphenanthrene-10-oxide (DOPO) to form the intermediate product of the following formula (II'):

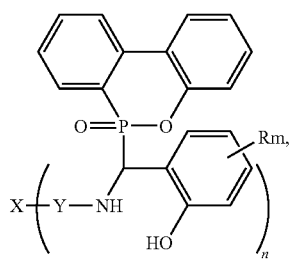

formula (II')

wherein X, Y, R, m and n are defined as described in the above formula (I), and subsequently formaldehyde or trioxymethylene is added to react with the intermediate product to obtain the final product.

According to the preparation method of the phosphorus-based oxazine compound in the present invention, the desired final product can be prepared in two-stage or in three-stage.

When n is 1 for formula (I), the phosphorus-based oxazine compound has a structure of the following formula (II):

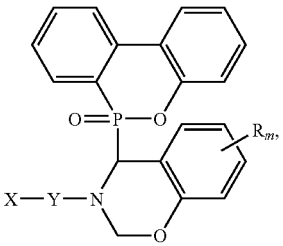

formula (II)

wherein X represents a hydrogen, a $C_1$-$C_6$ alkyl group, a $C_1$-$C_6$ alkyl group, a $C_1$-$C_6$ alkoxyl group, $CF_3$, $OCF_3$, a phenyl group, a halogen group, a phenoxy group or a $C_3$-$C_7$ cyclic alkyl group, Y represents

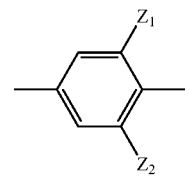

or a single bond, $Z_1$ or $Z_2$ individually represents a hydrogen, a $C_1$-$C_6$ alkyl group, a $C_1$-$C_6$ alkoxyl group, $CF_3$, a phenyl group, a halogen group, a phenoxy group or a $C_3$-$C_7$ cyclic alkyl group, m represents 1 or 2, R represents a hydrogen, a $C_1$-$C_6$ alkyl group, a $C_1$-$C_6$ alkoxyl group, $CF_3$, $OCF_3$, a phenyl group, a halogen group, a phenoxy group or a $C_3$-$C_7$ cyclic alkyl group, and when m is 2, R represents the same or different groups.

The two-stage method of preparing compounds of formula (II) comprises: contacting and mixing the following compounds

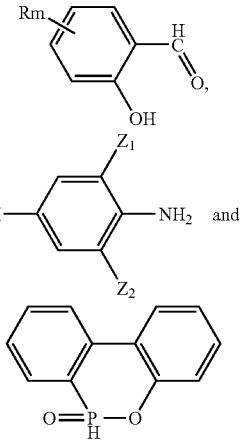

to form the intermediate product of the following formula (III):

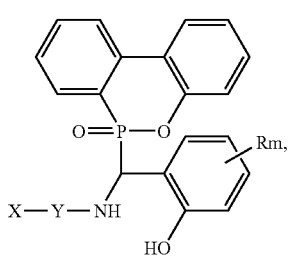

formula (III)

wherein X, Y, R and m are defined as described in the above formula (II), and subsequently adding formaldehyde or trioxymethylene to obtain the final product. The reaction is as follows:

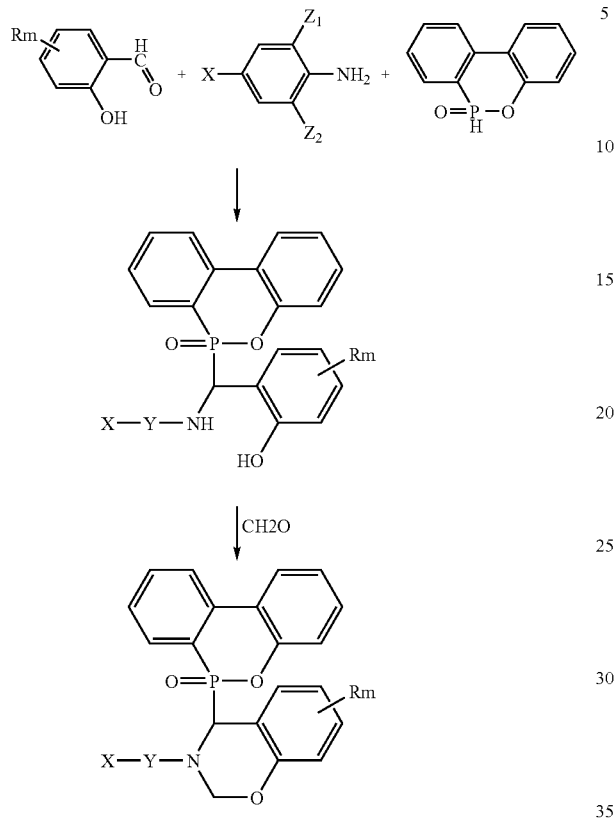

The three-stage method of preparing compounds of formula (II) comprises: contacting and mixing the following compounds:

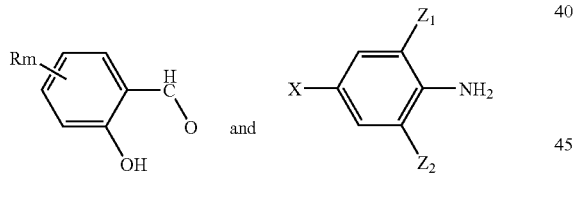

to form the intermediate product of the following formula (IV):

formula (IV)

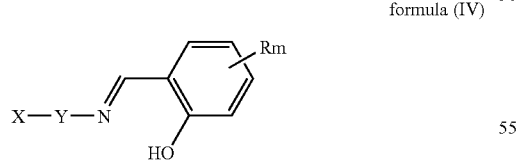

and subsequently adding the compound

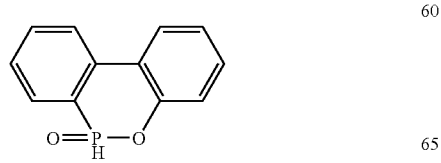

to form the intermediate product of formula (III):

formula (III)

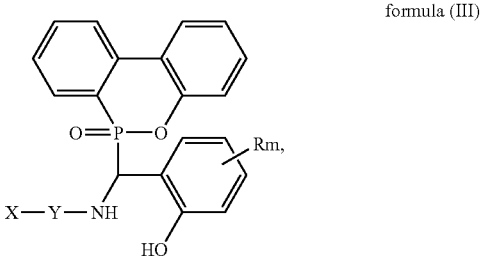

wherein X, Y, R and m are defined as described in the above formula (II), and then adding formaldehyde or trioxymethylene to obtain the final product. The reaction is as follows:

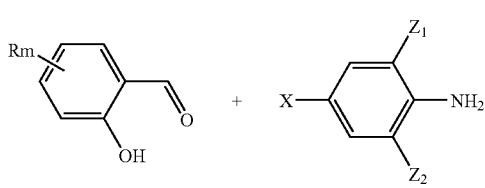

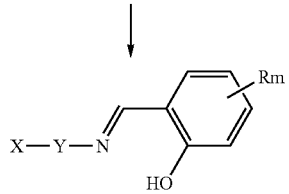

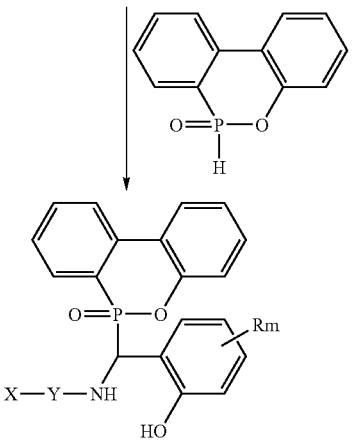

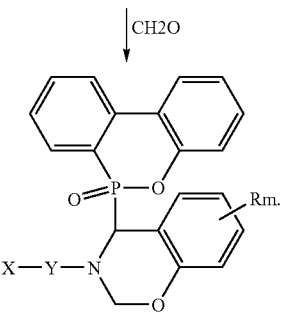

When n is 2 in formula (I), the phosphorus-based oxazine compound has a structure of the following formula (V):

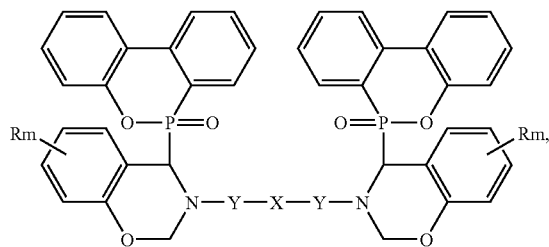

wherein X is the center of symmetry, for example, a single bond or selected from

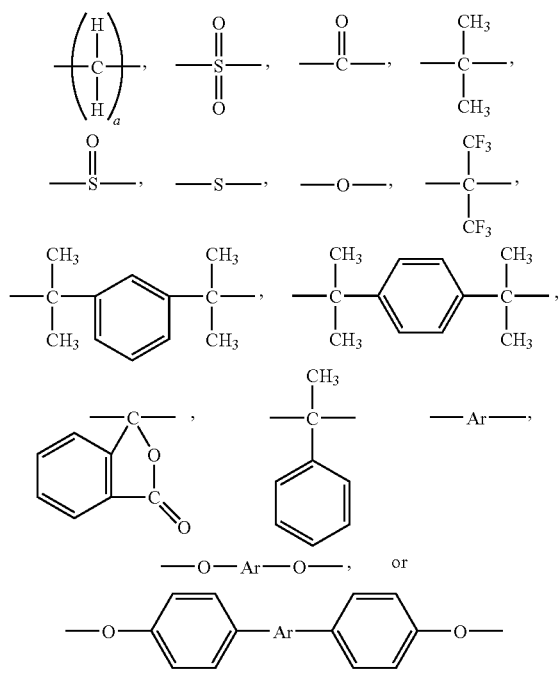

wherein a is an integer ranging from 1 to 16, Ar represents

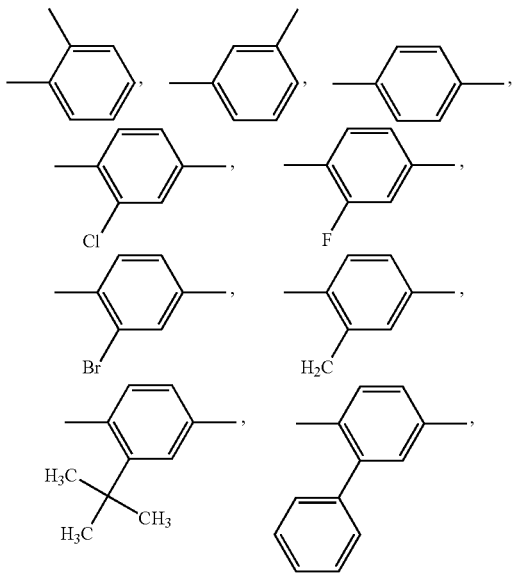

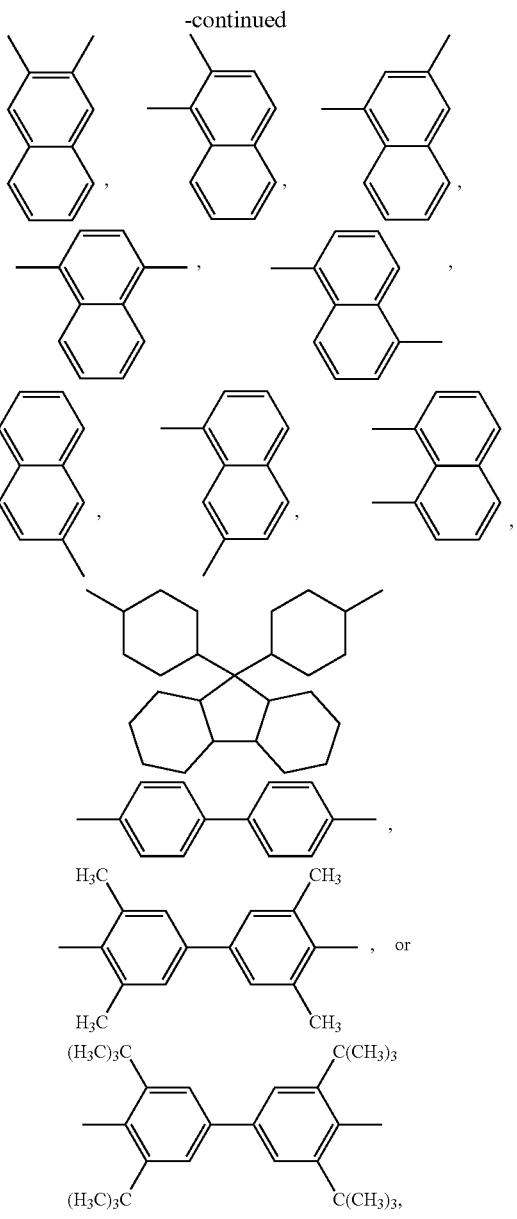

Y represents

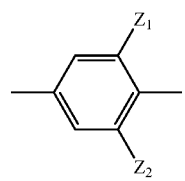

or a single bond, wherein $Z_1$ or $Z_2$ individually represents a hydrogen, a $C_1$-$C_6$ alkyl group, a $C_1$-$C_6$ alkoxyl group, $CF_3$, a phenyl group, a halogen group, a phenoxy group or a $C_3$-$C_7$ cyclic alkyl group, m represents 1 or 2, R represents a hydrogen, a $C_1$-$C_6$ alkyl group, a $C_1$-$C_6$ alkoxyl group, $CF_3$, $OCF_3$; a phenyl group, a halogen group, a phenoxy group or a $C_3$-$C_7$ cyclic alkyl group, and when m is 2, R represents the same or different groups.

The two-stage method of preparing compounds of formula (V) comprises: contacting and mixing the following compounds

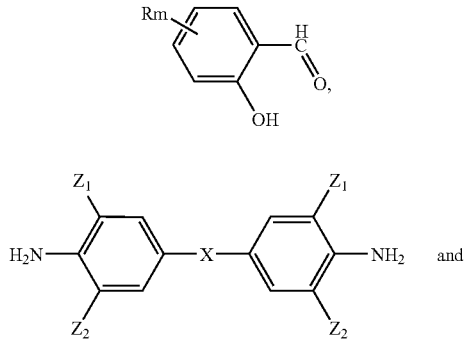

wherein X, Y, R and m are defined as described in the above formula (V), to form the intermediate product of the following formula (VI):

formula (VI)

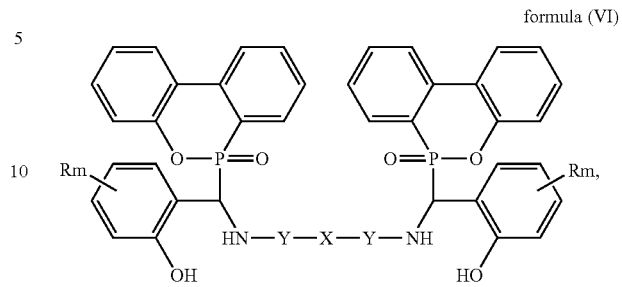

and subsequently adding formaldehyde or trioxymethylene to obtain the final product.

The reaction is as follows:

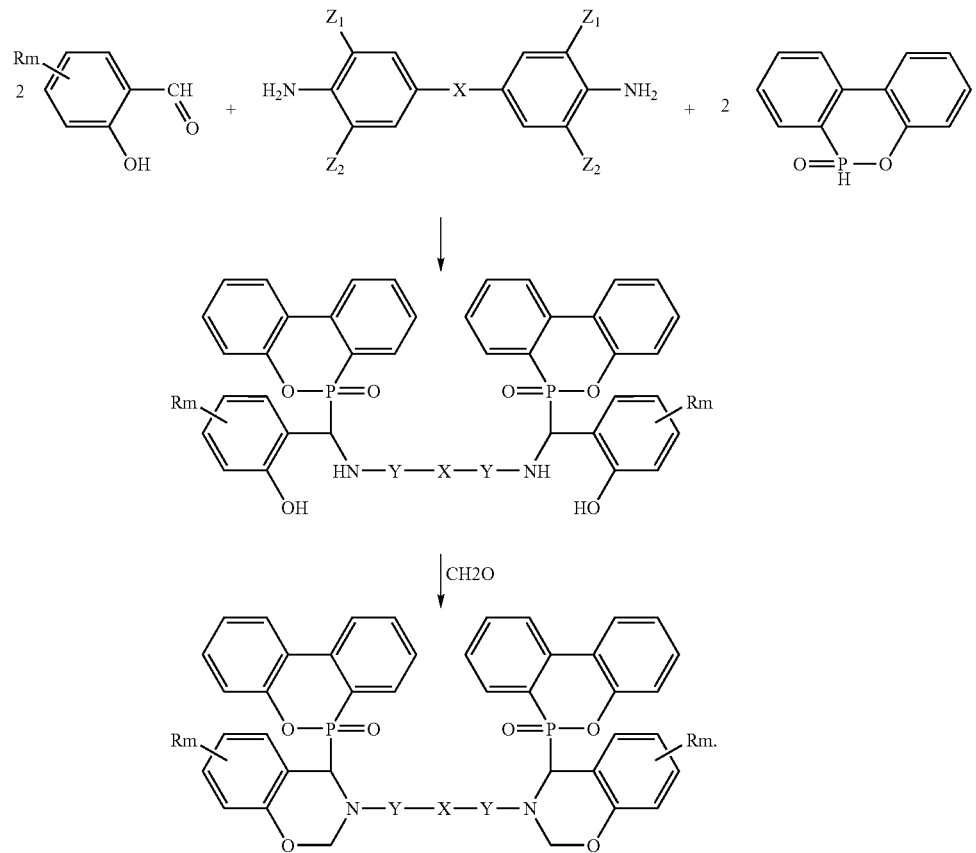

The three-stage method of preparing compounds of formula (V) comprises: contacting and mixing the following compounds:

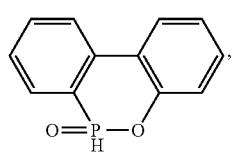

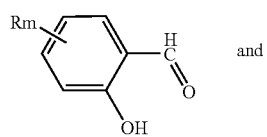 and

-continued

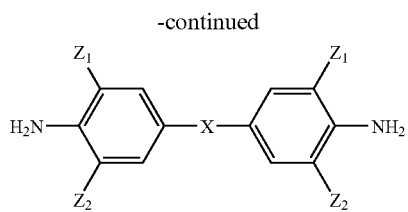

to form the intermediate product of the following formula (VII):

formula (VII)

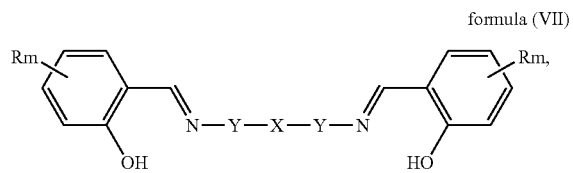

wherein X, Y, R and m are defined as described in the above formula (V), and later adding the compound

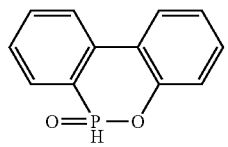

to form the intermediate product of formula (VI):

formula (VI)

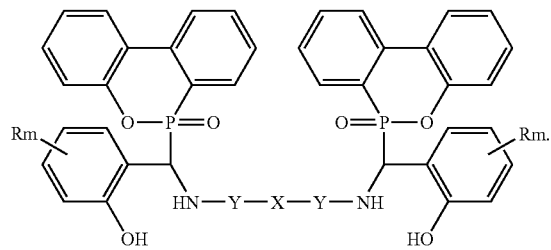

The reaction is as follows:

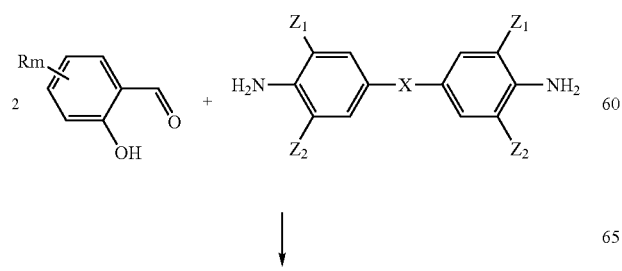

-continued

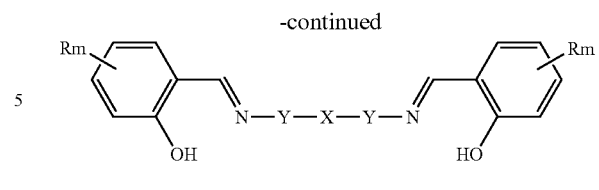

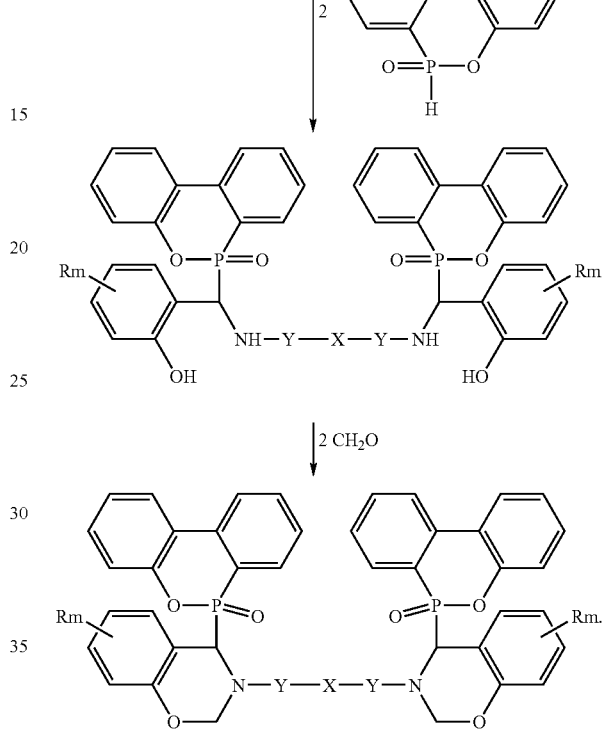

EXAMPLE 1

Two-Stage Synthesis of the Compound P-Aniline-Bz (Bz: benzoxazine)

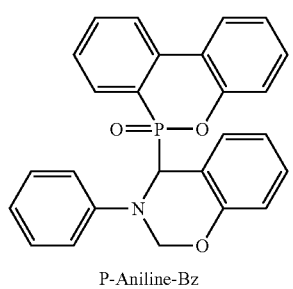

P-Aniline-Bz

Two-stage synthesis of the compound P-Aniline-Bz can be categorized as: Stage (I) Synthesis of the intermediate product P-Aniline-HB (HB: hydroxybenzaldehyde); Stage (II) Synthesis of P-Aniline-Bz. The reaction is as follows:

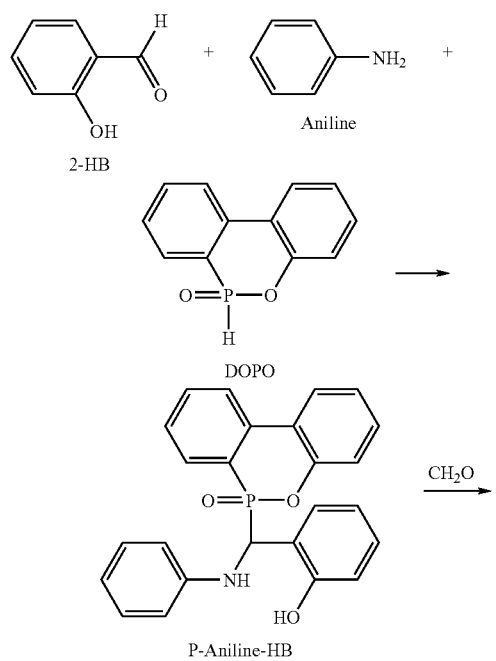

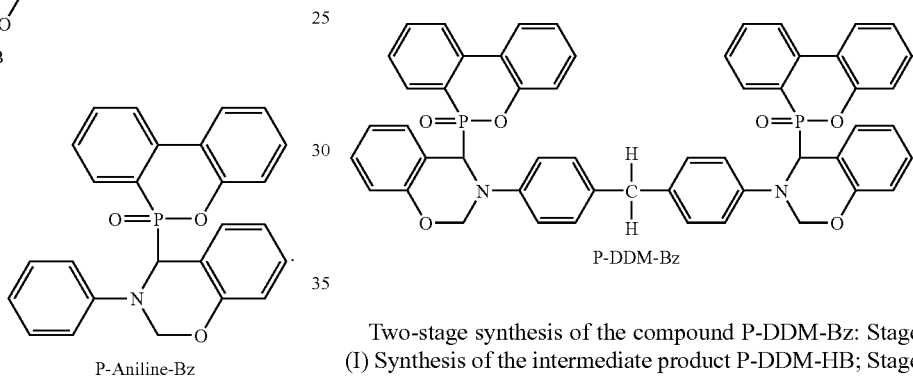

Stage (I): Synthesis of the intermediate product P-Aniline-HB. Add aniline 11.1688 g (120 mmol), 2-hydroxybenzaldehyde 14.6544 g (120 mmol) and DOPO 25.9404 g (120 mmol) to the flask containing 300 ml of dimethyl formamide (DMF), and keep stirring at room temperature for 12 hours. After the reaction completed, the solution is decanted into the saturated saline to obtain white precipitates. Following filtration and baking, 46.07 g white powder is obtained with a yield rate of 89%.

Stage (II) Synthesis of P-Aniline-Bz. After adding 12.402 g (30 mmol) of Stage (I) product to the flask containing 200 ml chloroform, 2.6775 g (33 mmol) of formaldehyde solution is added drop-wise to the flask, stirred at room temperature for 5 hours, heated to the reflux temperature and keep stirring for 12 hours. After the reaction completed, remove the solvents with the rotary evaporator and then white powder is obtained with a yield rate of 100%.

EXAMPLE 2

Two-Stage Synthesis of the Compound P-DDM-Bz
(DDM: 4,4'-diaminodiphenylmethane)

Two-stage synthesis of the compound P-DDM-Bz: Stage (I) Synthesis of the intermediate product P-DDM-HB; Stage (II) Synthesis of P-DDM-Bz. The reaction is as follows:

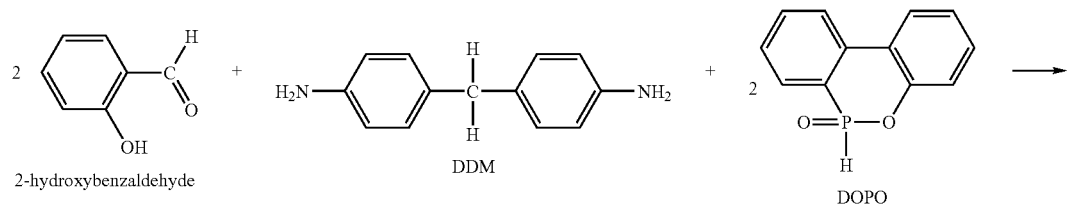

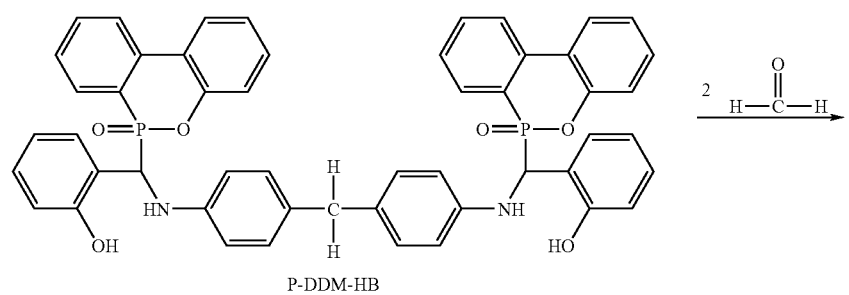

-continued

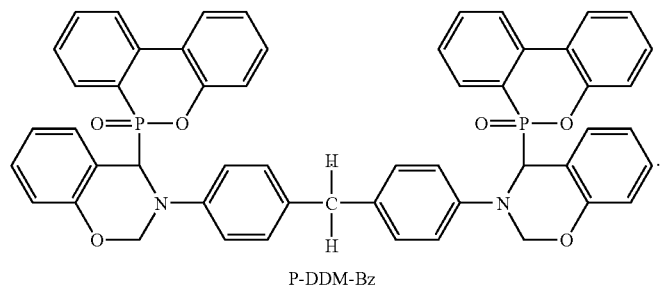

P-DDM-Bz

Figure 1B:
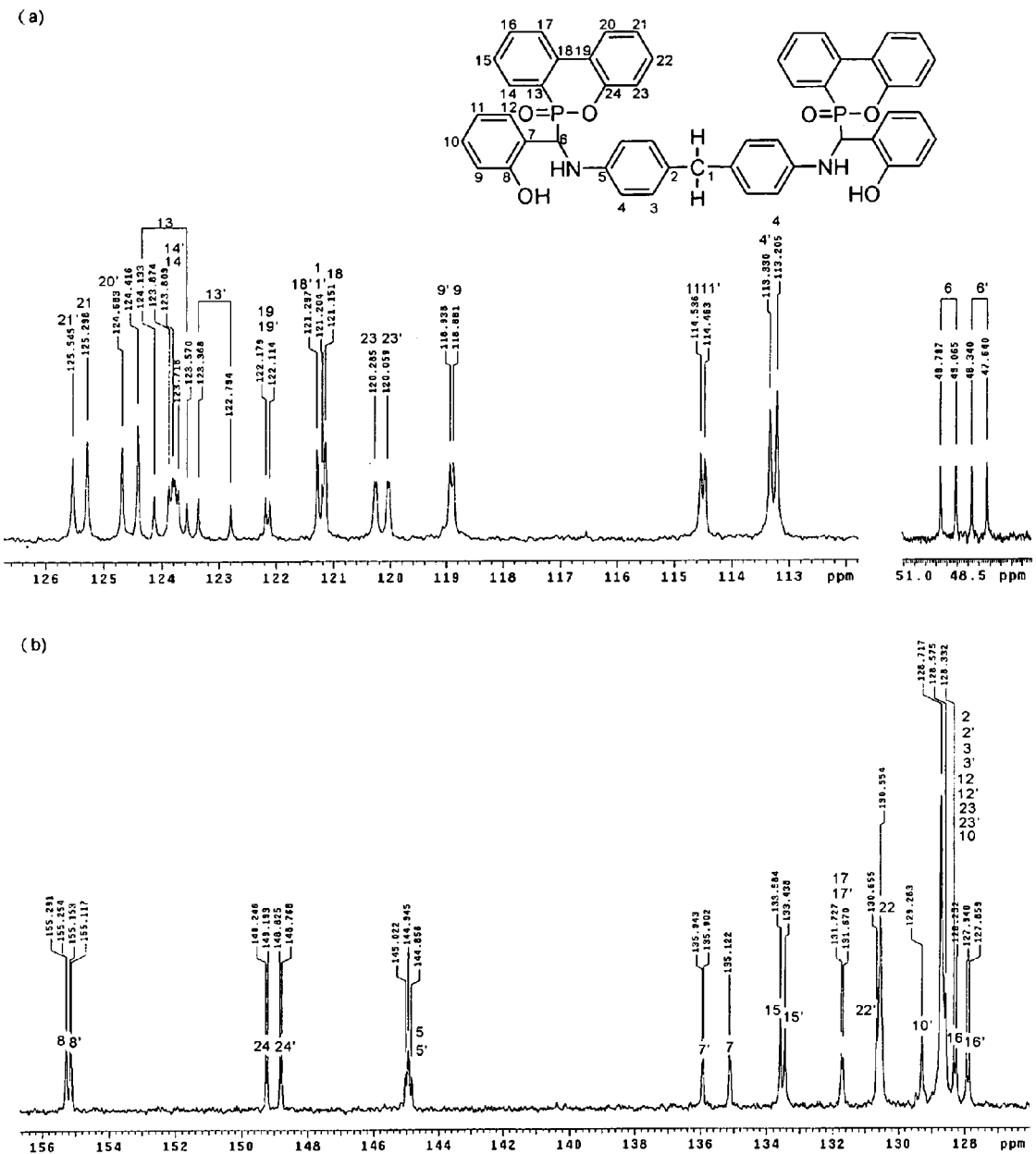

Stage (I) Synthesis of the intermediate product P-DDM-HB. DDM (4,4'-diaminodiphenylmethane) 11.8956 g (60 mmol), 2-hydroxybenzaldehyde (2-hydroxybenzaldehyde, 2-HB) 14.6544 g (120 mmol) and DOPO 25.94 g (120 mmol) are added to the flask containing 300 ml DMF, and keep stirring at room temperature for 12 hours. After the reaction completed, the solution is poured into water to obtain white precipitates. Following filtration and baking, 46.54 g green powder is obtained with a yield rate of 92%. The results are shown in FIG. 1A, 1B. FIG. 1A and FIG. 1B are respectively 1H-NMR and 13C-NMR spectrums of the intermediate product P-DDM-HB. Because phosphorus (P) and the aliphatic carbon(s) connected to P are chiral centers, the compound P-DDM-HB includes two diastereomers (either RR (or SS) and RS (or SR) conformational isomers). Therefore, two sets of peaks are present in the spectrum. The structure of the synthesized P-DDM-HB can be verified from the figures.

Figure 1C:
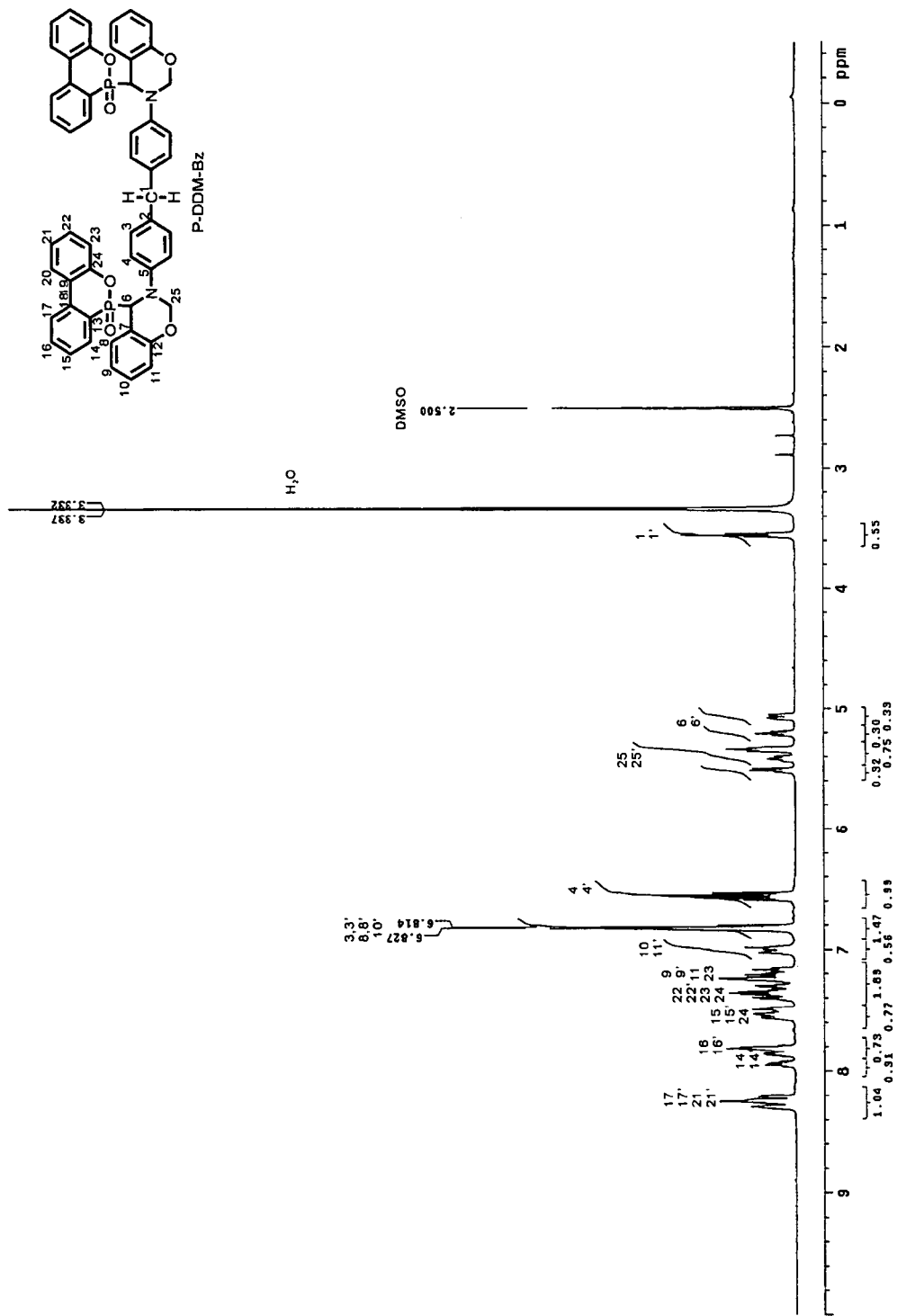
FIG. 1C and FIG. 1D are respectively 1H-NMR and 13C-NMR spectrums of the compound P-DDM-Bz according to the example 2 of this invention.
Figure 1D:
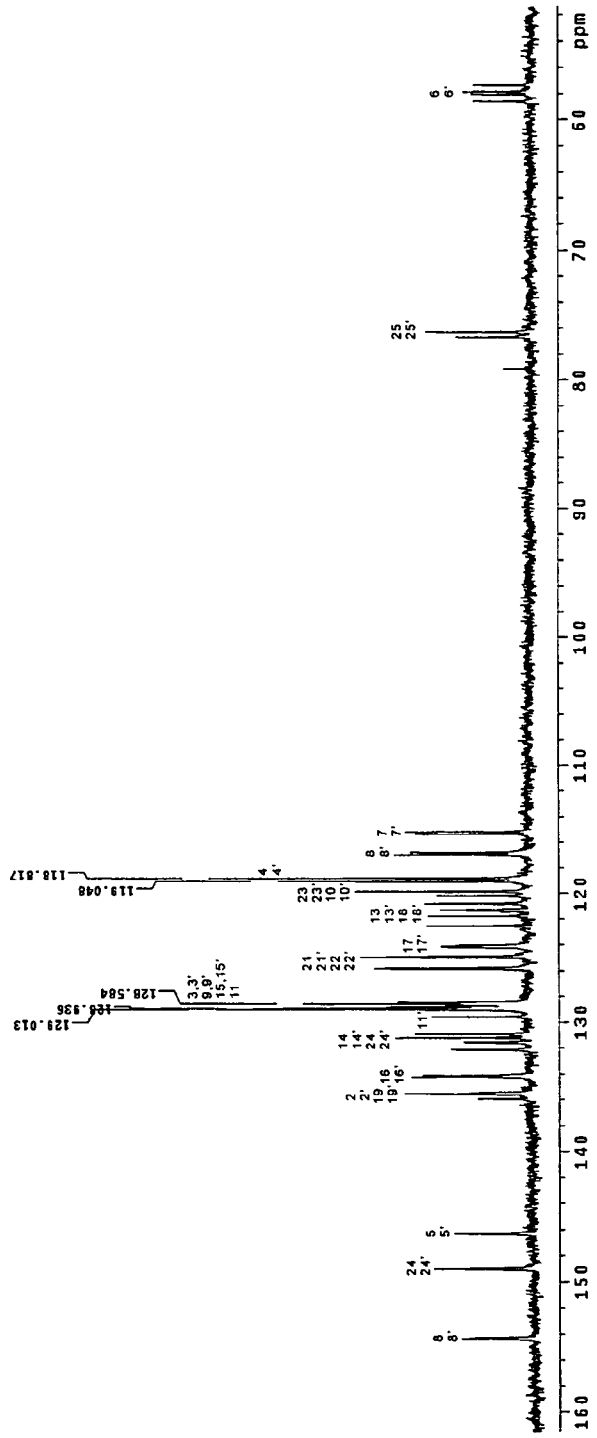

Stage (II) Synthesis of P-DDM-Bz. After adding 25.1646 g (30 mmol) of P-DDM-HB to the flask containing 200 ml chloroform, 5.3549 g (66 mmol) of formaldehyde solution is added drop-wise to the flask. The mixture is stirred at room temperature for 5 hours, heated to the reflux temperature and keeps stirring for 12 hours. After the reaction completed, remove the solvents with the rotary evaporator, baking in the vacuum oven and then brown powder is obtained with a yield rate of 100%. The results are shown in FIG. 1C and FIG. 1D. FIGS. 1C and 1D are 1H-NMR spectrum and 13C-NMR spectrum of the product P-DDM-Bz. Because phosphorus (P) and the aliphatic carbon(s) connected to P are chiral centers, the compound P-DDM-Bz includes two diastereomers (RR (or SS) and RS (or SR) conformational isomers). Therefore, two sets of peaks are present in the spectrum. The structure of the synthesized P-DDM-Bz can be verified from the figures.

EXAMPLE 3

Two-Stage Synthesis of the Following Compound P-BAPP-BZ (BAPP: 2,2'-Bis[4-(4-aminophenoxy) phenyl]propane)

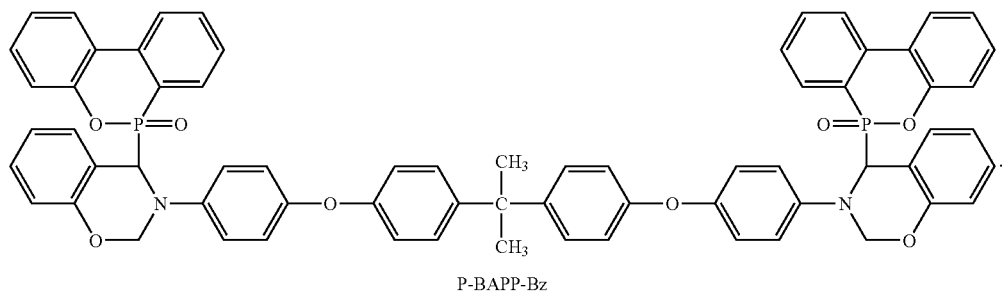

P-BAPP-Bz

Two-stage synthesis of P-BAPP-BZ, Stage (I) Synthesis of the intermediate product P-BAPP—HB; Stage (II) Synthesis of the monomer P-BAPP-BZ. The reaction is as follows:

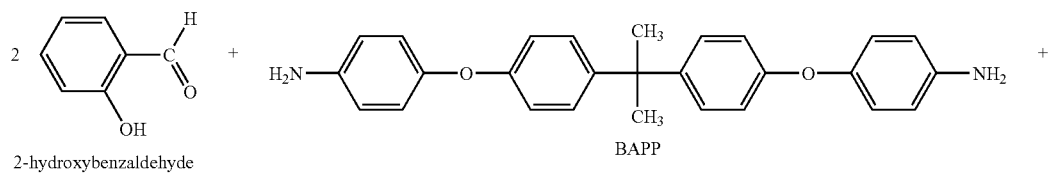

2-hydroxybenzaldehyde      BAPP

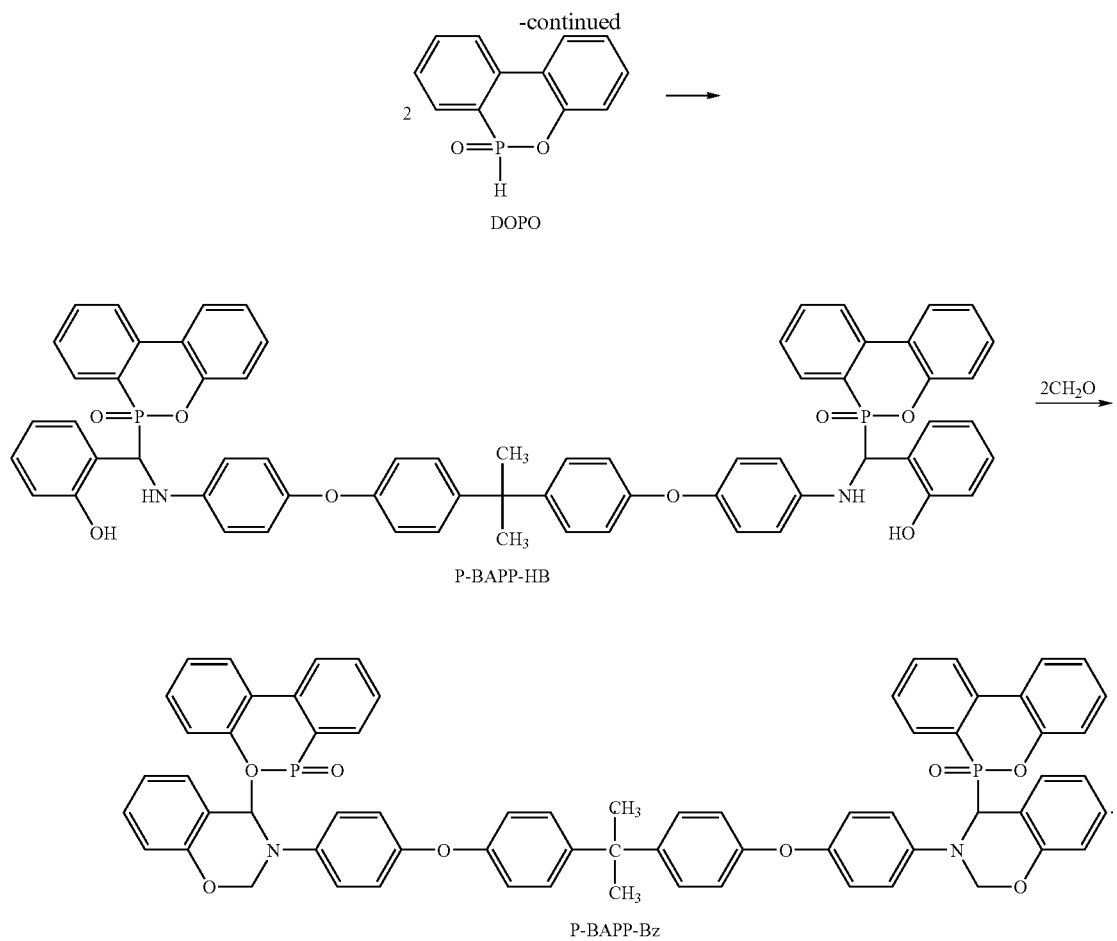

P-BAPP-Bz

Figure 2A:
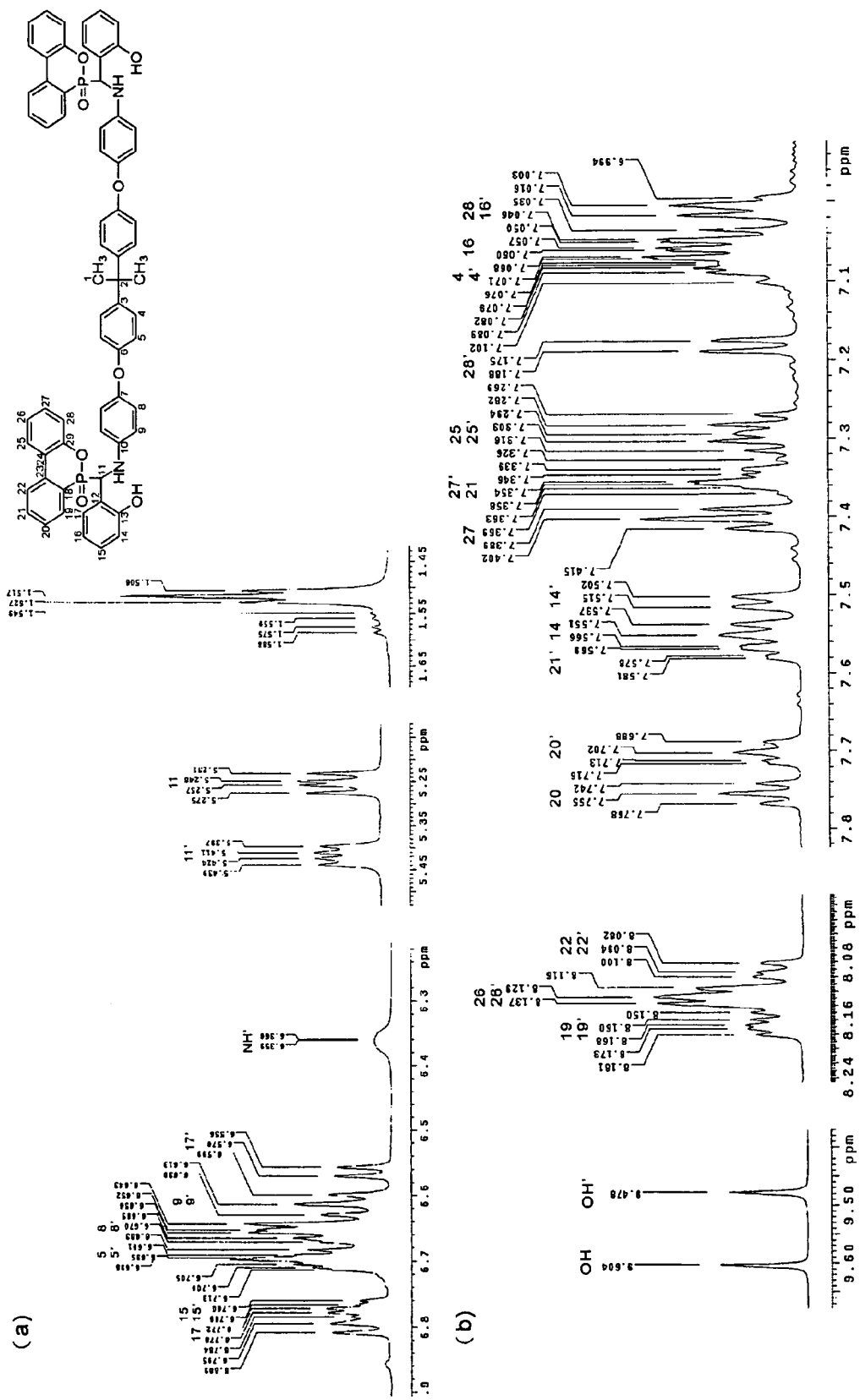
FIG. 2A and FIG. 2B are respectively 1H-NMR and 13C-NMR spectrums of the intermediate compound P-BAPP—HB according to the example 3 of this invention.
Figure 2B:
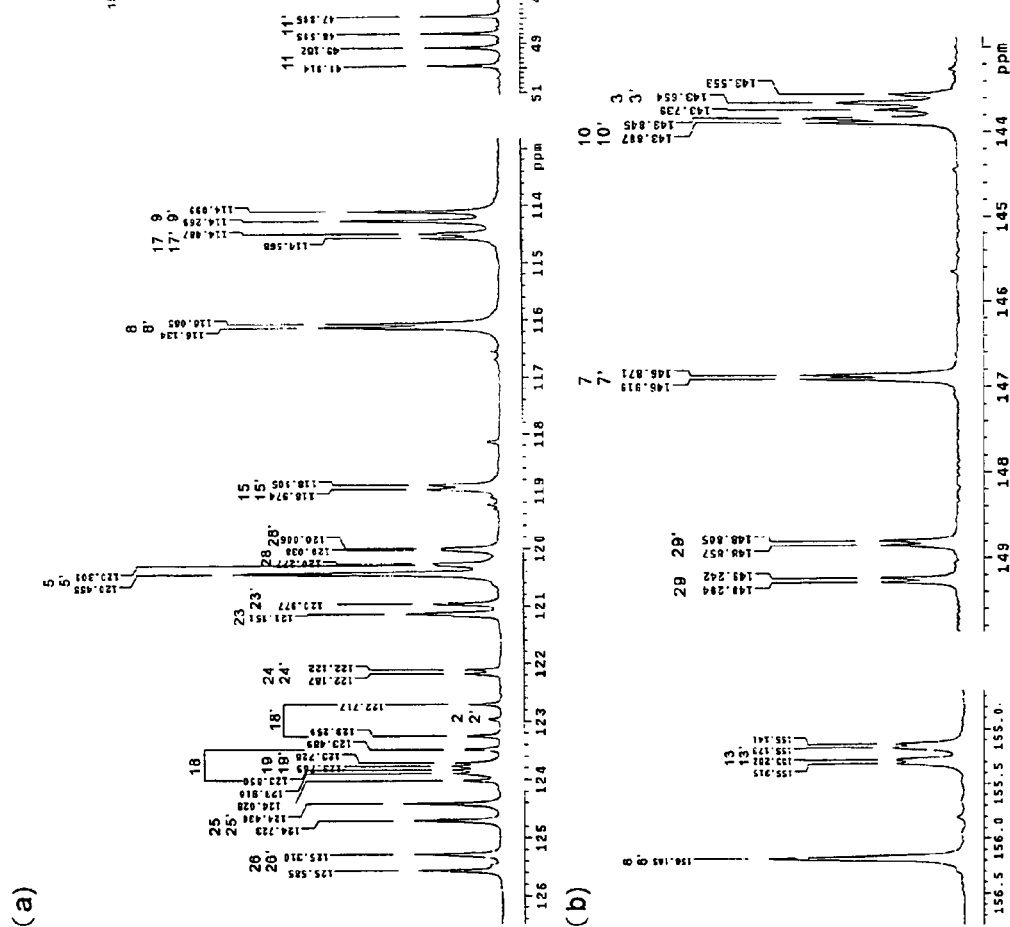

Stage (I) Synthesis of the intermediate product P-BAPP—HB. BAPP (2,2'-Bis[4-(4-aminophenoxy)phenyl]propane) 24.6306 g (60 mmol), 2-HB 14.6544 g (120 mmol) and DOPO 25.9404 g (120 mmol) are added to the flask containing 300 ml DMF, and keep stirring at room temperature for 12 hours. After the reaction completed, the solution is poured into water to obtain precipitates. Following filtration and baking, 60.12 g light yellow powder is obtained with a yield rate of 95%. The results are shown in FIG. 2A and FIG. 2B. FIGS. 2A and 2B are 1H-NMR spectrum and 13C-NMR spectrum of the intermediate product P-BAPP—HB. Because phosphorus (P) and the aliphatic carbon(s) connected to P are chiral centers, the compound P-BAPP—HB includes two diastereomers (RR (or SS) and RS (or SR) conformational isomers). Therefore, two sets of peaks are present in the spectrum. The structure of the synthesized P-BAPP—HB can be verified from the figures.

Figure 2C:
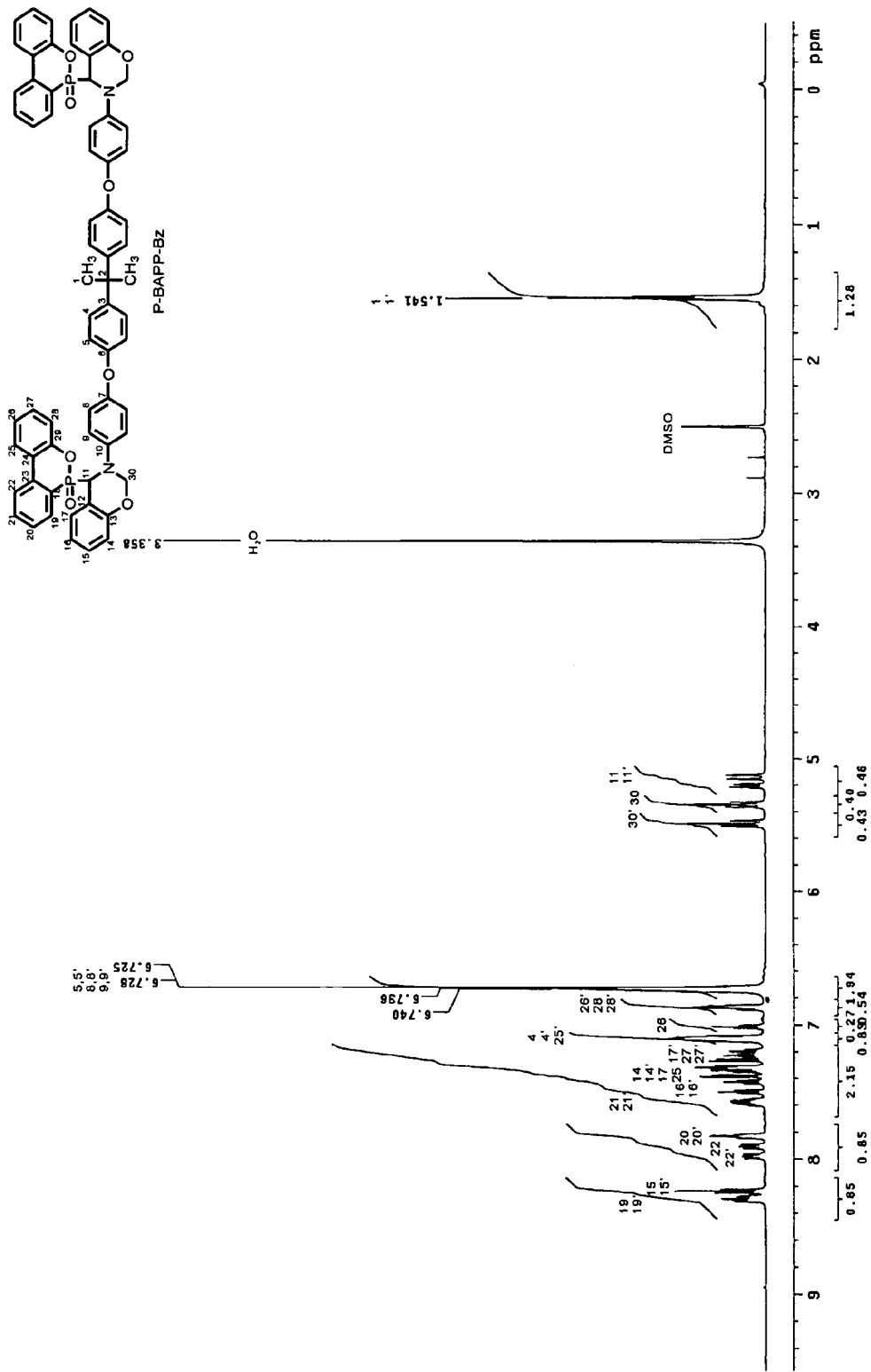
FIG. 2C and FIG. 2D are respectively 1H-NMR and 13C-NMR spectrums of the compound P-BAPP-Bz according to the example 3 of this invention.
Figure 2D:
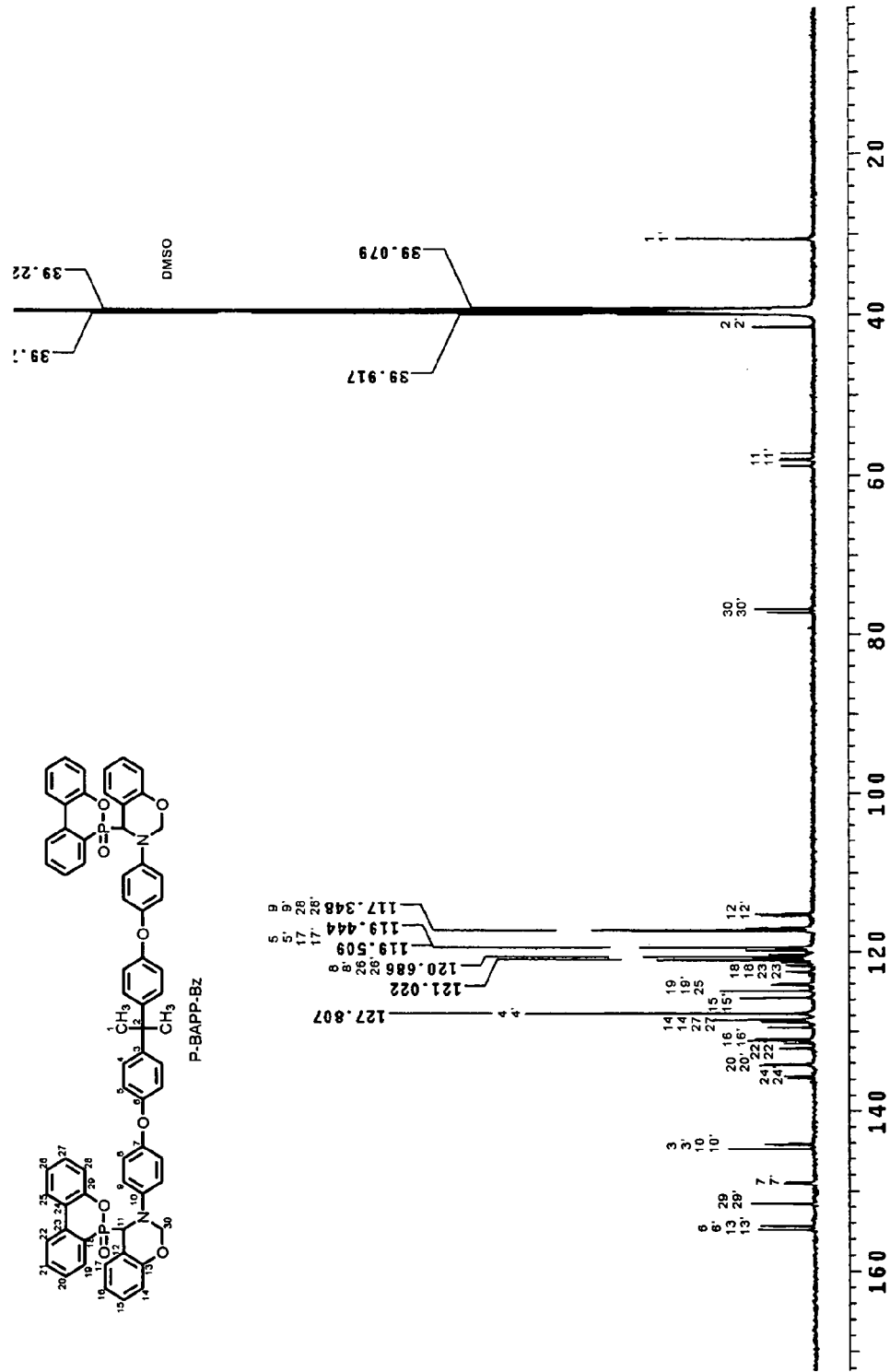

Stage (II) Synthesis of the monomer P-BAPP-Bz. After adding 21.021 g (20 mmol) of P-BAPP—HB to the flask containing 150 ml chloroform, 3.57 g (44 mmol) of formaldehyde solution is drop-wise added to the flask. The mixture is stirred at room temperature for 5 hours, heated to the reflux temperature and keep stirring for 12 hours. After the reaction completed, remove the solvents with the rotary evaporator, baking in the vacuum oven and then yellow powder P-BAPP-Bz is obtained with a yield rate of 100%. The results are shown in FIG. 2C and FIG. 2D. FIGS. 2C and 2D are 1H-NMR spectrum and 13C-NMR spectrum of the product P-BAPP-Bz. Because phosphorus (P) and the aliphatic carbon(s) connected to P are chiral centers, the compound P-BAPP-Bz includes two diastereomers (RR (or SS) and RS (or SR) conformational isomers). Therefore, two sets of peaks are present in the spectrum. The structure of the synthesized P-BAPP-Bz can be verified from the figures.

EXAMPLE 4

Two-Stage Synthesis of the Compound P-DDS-Bz (DDS: 4,4'-Diaminodiphenyl sulfone)

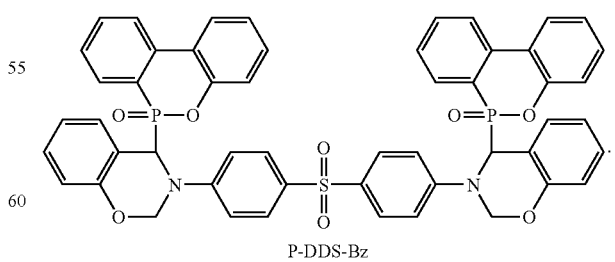

P-DDS-Bz

Two-stage synthesis of P-DDS-Bz: Stage (II) Synthesis of the intermediate product P-DDS-HB; Stage (II) Synthesis of P-DDS-Bz. The reaction is as follows:

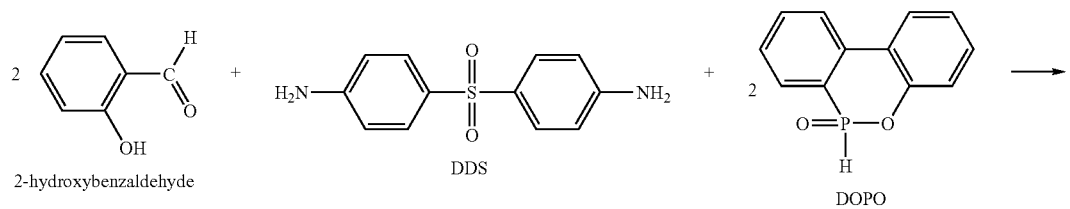

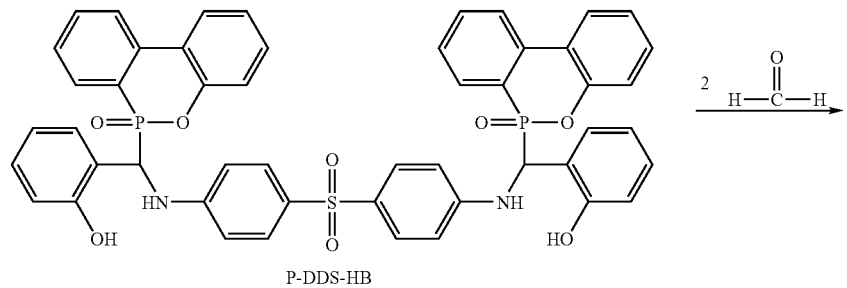

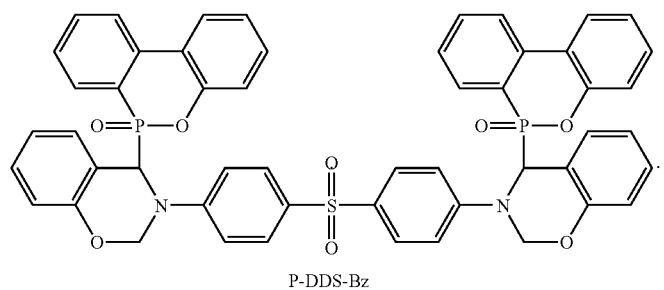

Stage (I) Synthesis of the intermediate product P-DDS-HB. DDS(4,4'-Diaminodiphenyl sulfone) 14.898 g (60 mmol), 2-HB 14.6544 g (120 mmol) and DOPO 25.9404 g (120 mmol) are added to the flask containing 300 ml DMF, and keep stirring at room temperature for 12 hours. Until the reaction completed, the solution is poured into the saturated saline to obtain white precipitates. Following filtration and baking, 44.97 g white powder is obtained with a yield rate of 84%.

Stage (II) Synthesis of P-DDS-Bz. 26.6658 g (30 mmol) of P-DDS-HB is added to the flaks containing 200 ml chloroform, then added drop-wise 5.3549 g (66 mmol) of formaldehyde solution to the flask, stirred at room temperature for 5 hours, heated to the reflux temperature and keeps stirring for 12 hours. After the reaction completed, remove the solvent with the rotary evaporator to obtain white powder P-DDS-Bz with a yield rate of 100%.

EXAMPLE 5

Three-Stage Synthesis of the Compound P—$C_2$-Bz

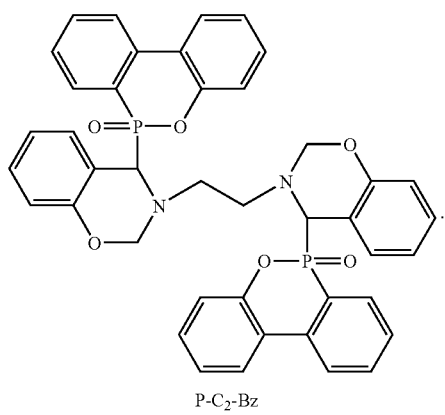

P-$C_2$-Bz

Three-stage synthesis of P—$C_2$-Bz: Stage (I) Synthesis of the intermediate product $C_2$—HB; Stage (II) Synthesis of the intermediate product P—$C_2$—HB; Stage (III) Synthesis of the monomer P—$C_2$-Bz. The reaction is as follows:

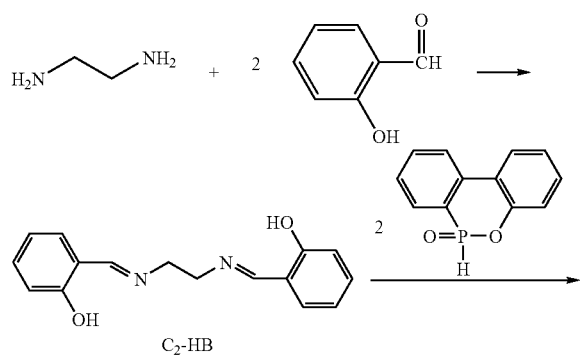

Figure 3A:
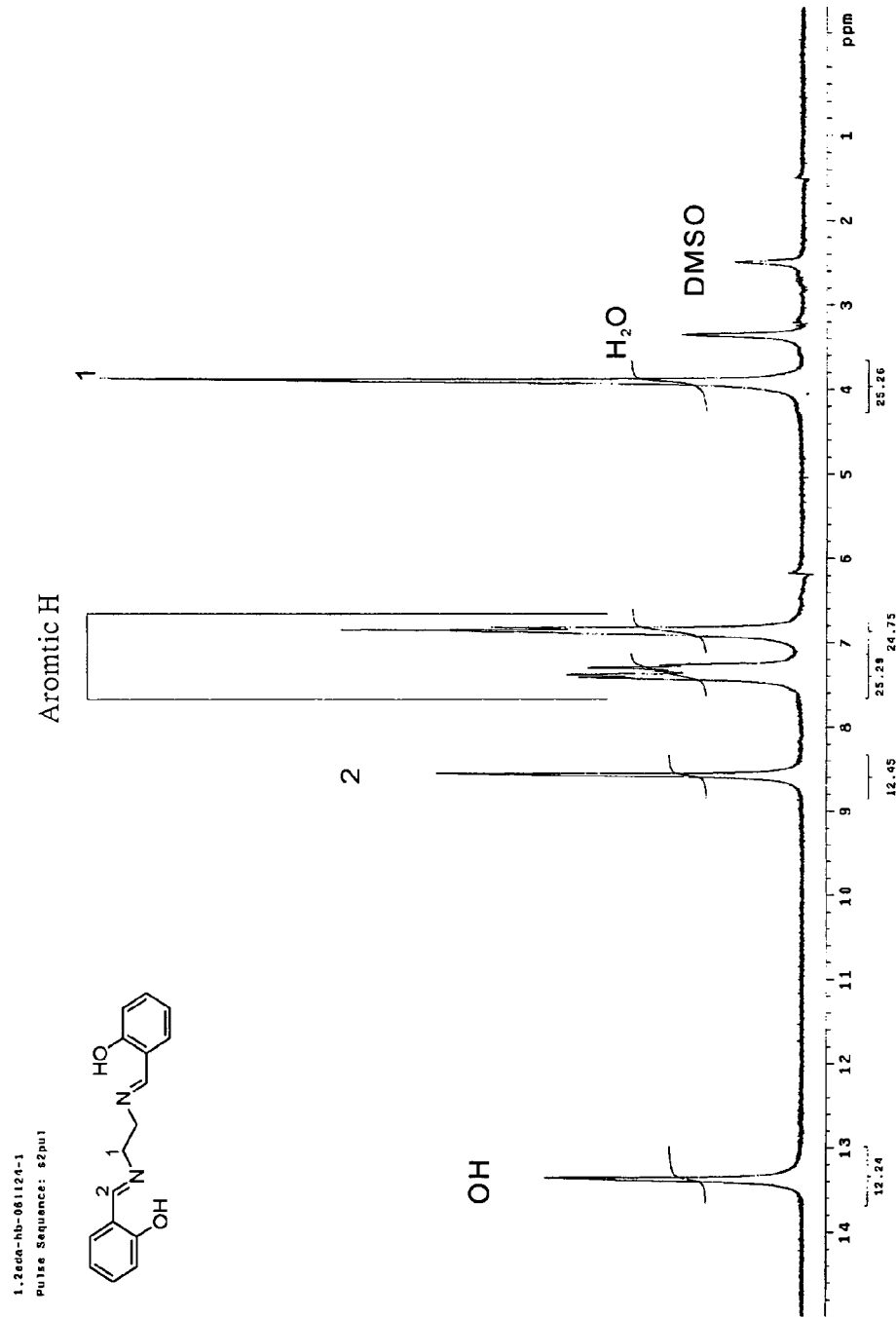
FIG. 3A is 1H-NMR spectrum of the intermediate compound $C_2$—HB according to the example 5 of this invention.

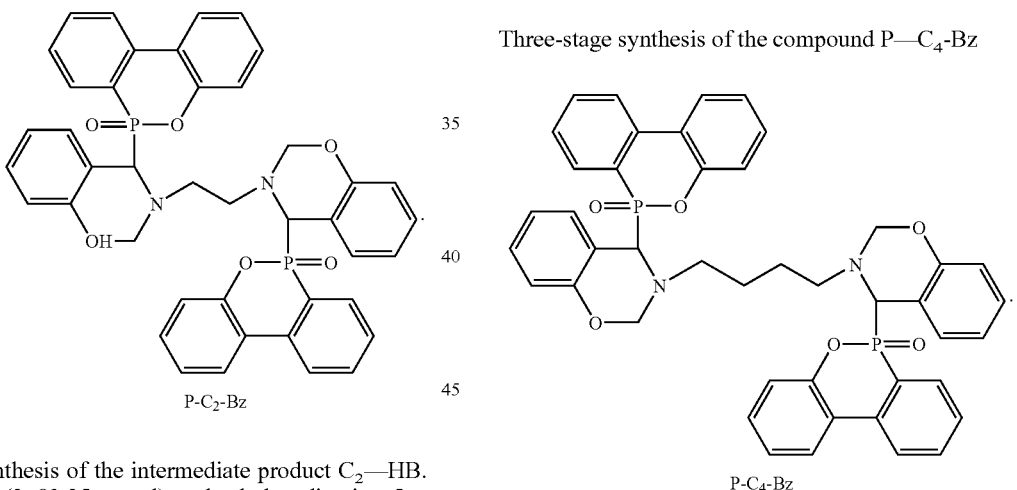

at 100° C., 21.6273 g yellow powder $C_2$—HB is obtained with a yield rate of 96.8%. Melting point 127.67° C. The results are shown in FIG. 3A. FIG. 3A is 1H-NMR spectrum of the intermediate product $C_2$—HB. The structure of the synthesized $C_2$—HB can be verified by the figure.

Figure 3B:
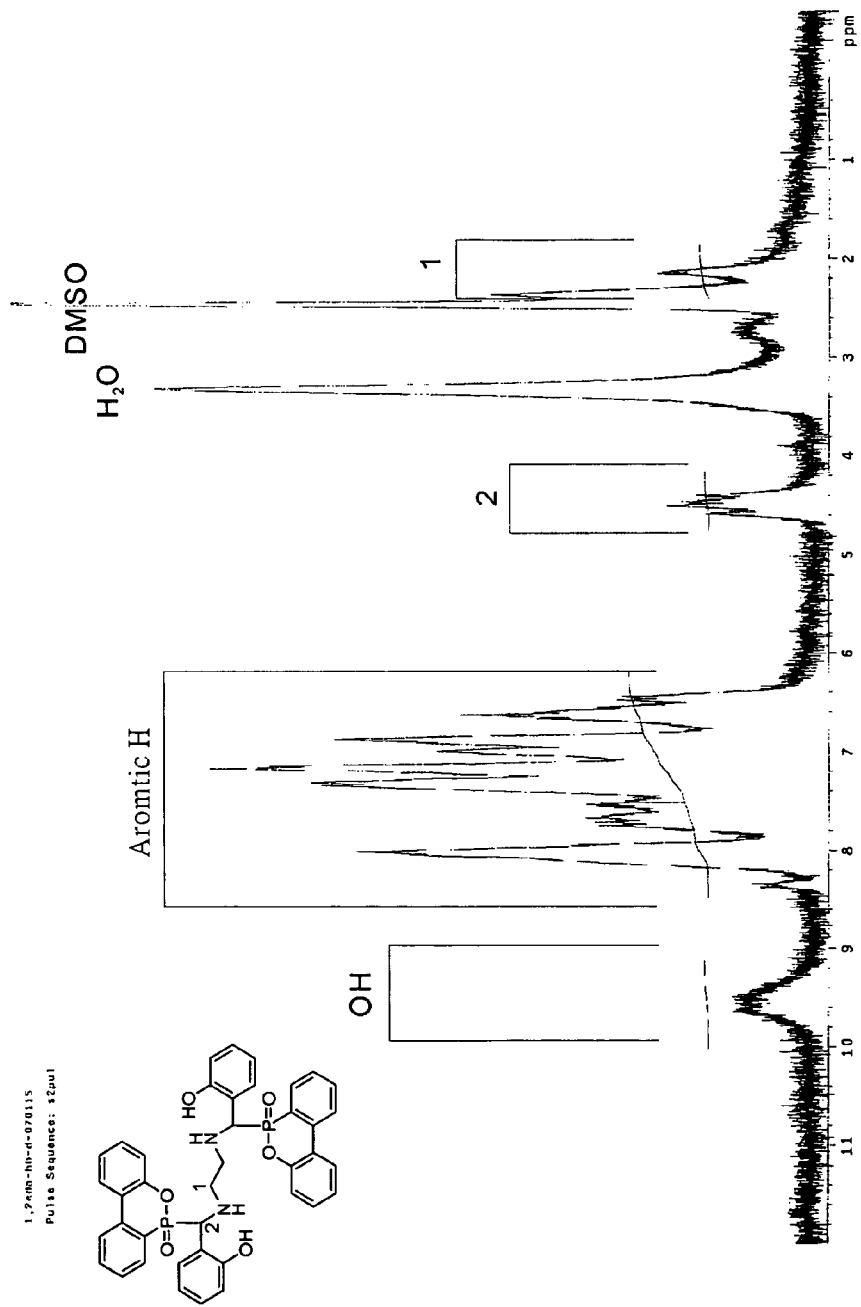
FIG. 3B is 1H-NMR spectrum of the intermediate compound P—$C_2$—HB according to the example 5 of this invention.

Next, Stage (II) Synthesis of the monomer P—$C_2$—HB. 5 g (18.65 mmol) of $C_2$—HB is dissolved in 30 ml ethanol within a 100 ml three-neck flask. After adding DOPO 8.058 g (18.65×2 mmol) to the three-neck flask, the mixture is stirred at room temperature for 12 hours. The mixture is poured into de-ionized water to form yellow powder precipitates. After filtration, vacuum evaporation and baking, 12.6214 g light yellow powder P—$C_2$—HB is obtained with a yield rate of 96.7%. The results are shown in FIG. 3B. FIG. 3B is 1H-NMR spectrum of the intermediate product P—$C_2$—HB. The structure of the synthesized P—$C_2$—HB can be verified by the figure.

Figure 3C:
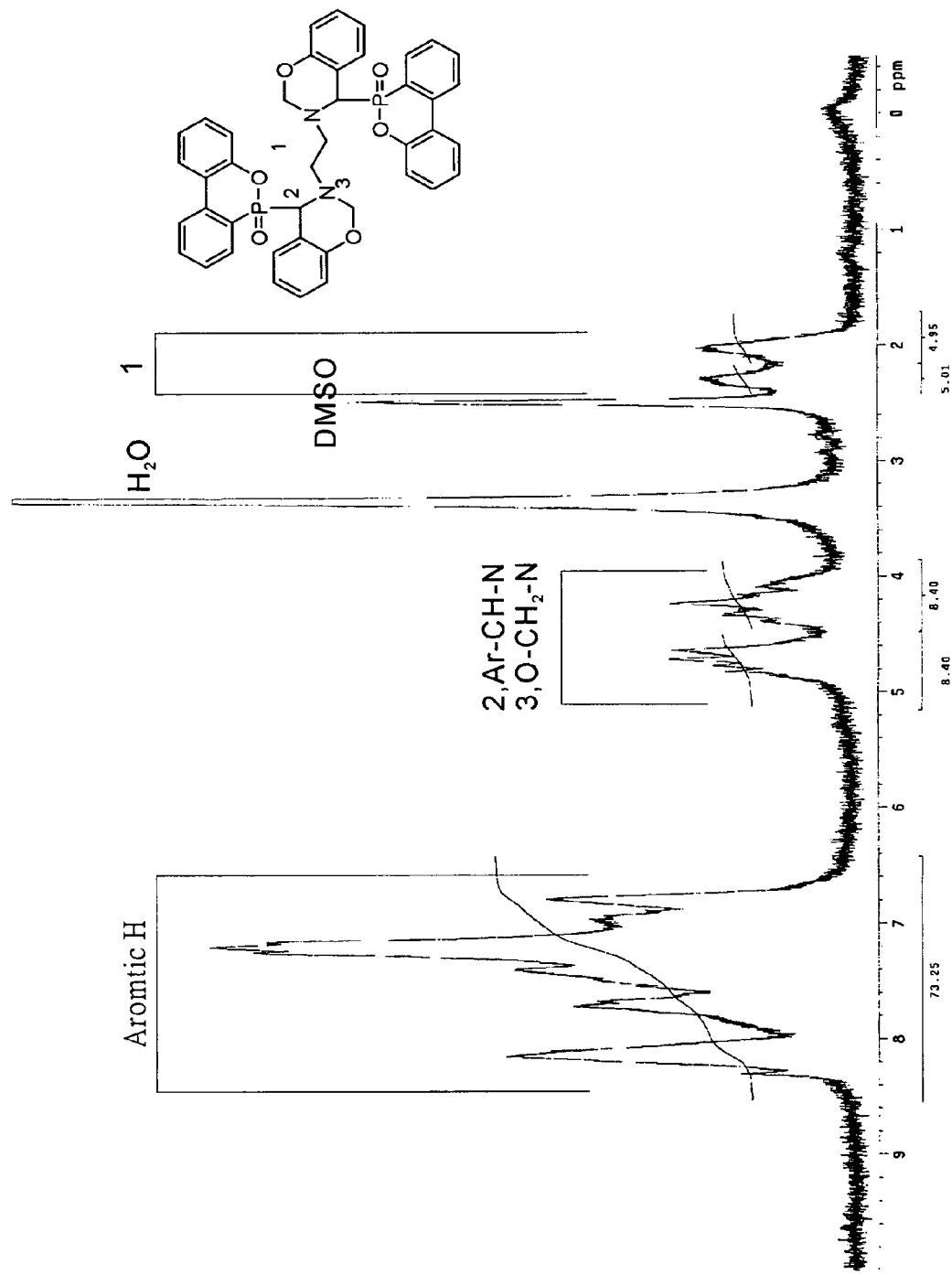
FIG. 3C is 1H-NMR spectrum of the compound P—$C_2$-Bz according to the example 5 of this invention.

Stage (III) Synthesis of the monomer P—$C_2$-Bz. 5 g (14.3 mmol) of P—$C_2$—HB is dissolved in 10 ml chloroform within a 100 ml three-neck flask. 1.16 g (14.3×2 mmol) of formaldehyde solution (37%) is added drop-wise to the three-neck flask. The mixture is stirred at room temperature (35° C.) for 1 hour, heated to the reflux temperature and keep stirring for 10 hours. The mixture is dried by the rotary evaporator to obtain light yellow powder P—$C_2$-Bz. The results are shown in FIG. 3C. FIG. 3C is 1H-NMR spectrum of the product P—$C_2$-Bz. The structure of the synthesized P—$C_2$-Bz can be verified by the figure.

EXAMPLE 6

Three-stage synthesis of the compound P—$C_4$-Bz

Stage (I) Synthesis of the intermediate product $C_2$—HB. 2-HB 20.32 g (2×83.25 mmol) and ethylenediamine 5 g (83.25 mmol) are dissolved in 50 ml DMF within a three-neck flask and stirred under nitrogen until slightly exothermic. Under room temperature, the mixture keeps stirring for 6 hours. The mixture is poured into de-ionized water for precipitates. After vacuum filtration and baking by vacuum oven Three-stage synthesis of P—$C_4$-Bz: Stage (I) Synthesis of the intermediate product $C_4$—HB; Stage (II) Synthesis of the intermediate product P—$C_4$—HB; Stage (III) Synthesis of the monomer P—$C_4$-Bz. The reaction is as follows:

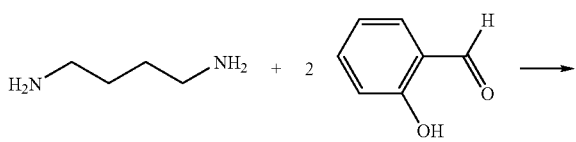

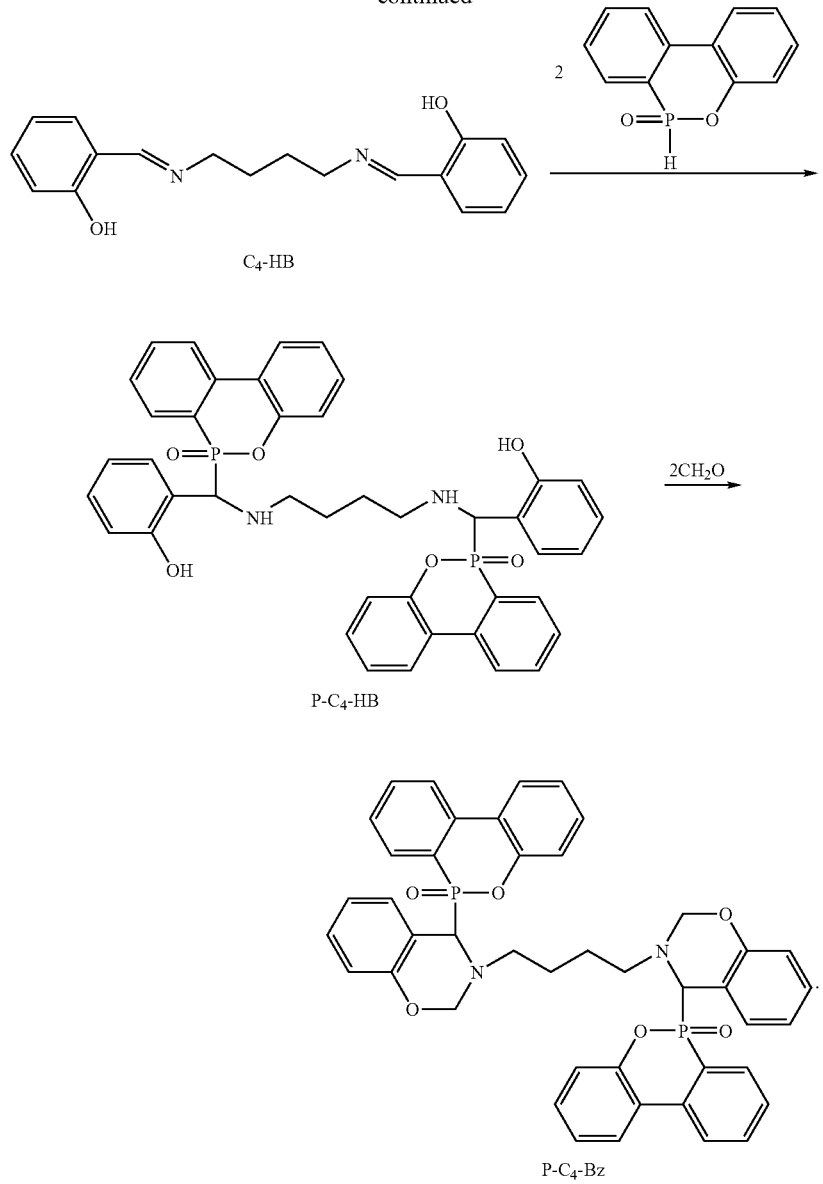

Figure 4A:
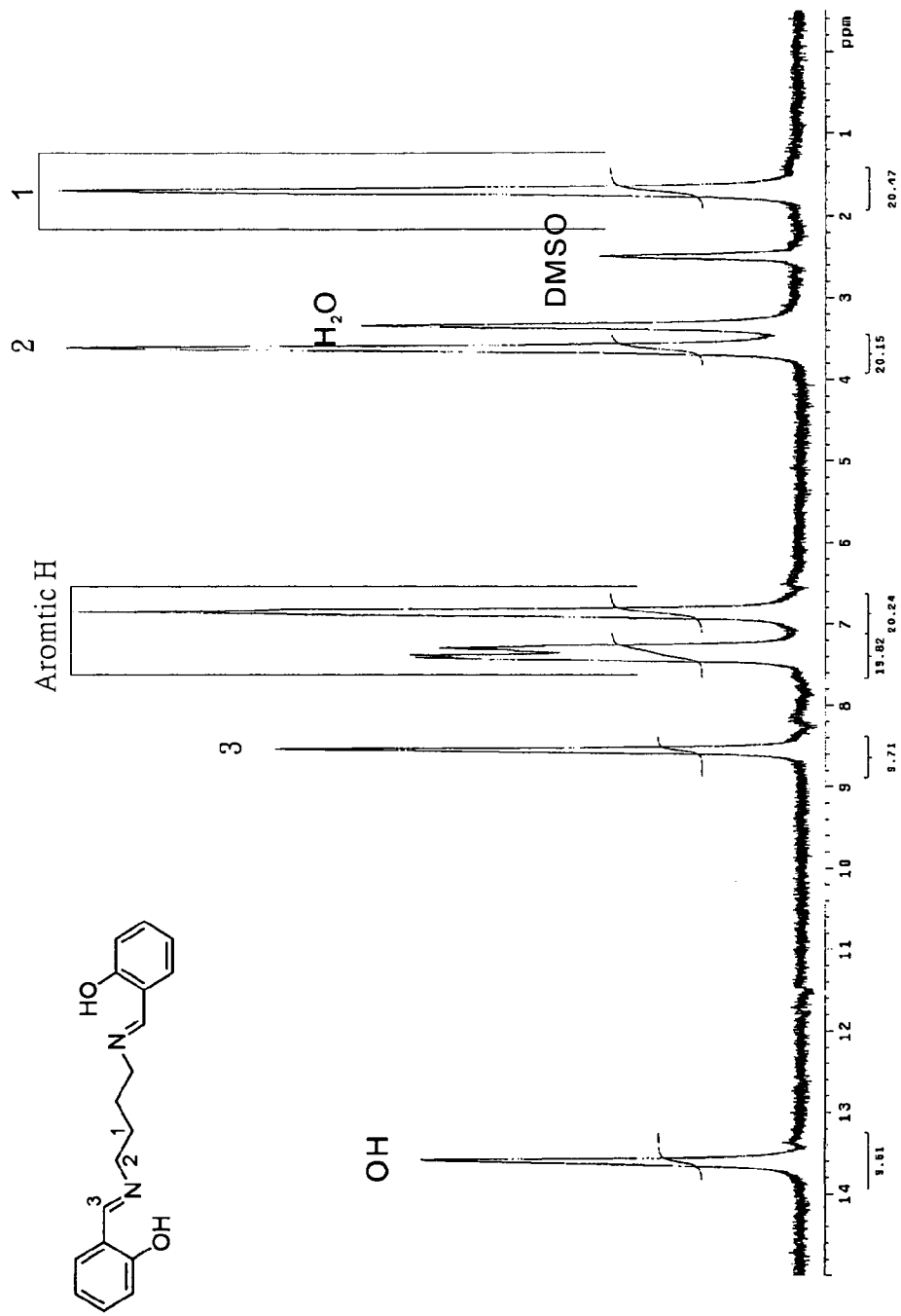
FIG. 4A is 1H-NMR spectrum of the intermediate compound $C_4$—HB according to the example 6 of this invention.

Stage (I) Synthesis of the intermediate product C$_4$—HB. 2-HB 13.8515 g (56.75×2 mmol) and 1,4-butanediamine 5 g (56.75 mmol) are dissolved in 50 ml DMF within a three-neck flask, and stirred under nitrogen until slightly exothermic. Under room temperature, keep stirring for 6 hours for maximum precipitates. The mixture is poured into de-ionized water for precipitates. After filtration, vacuum evaporation and vacuum oven at 70° C., 21.6273 g yellow powder 4-HB is obtained with a yield rate of 96.8%. Melting point 91° C. The results are shown in FIG. 4A. FIG. 4A is 1H-NMR spectrum of the intermediate product C$_4$—HB. The structure of the synthesized C$_4$—HB can be verified by the figure.

Figure 4B:
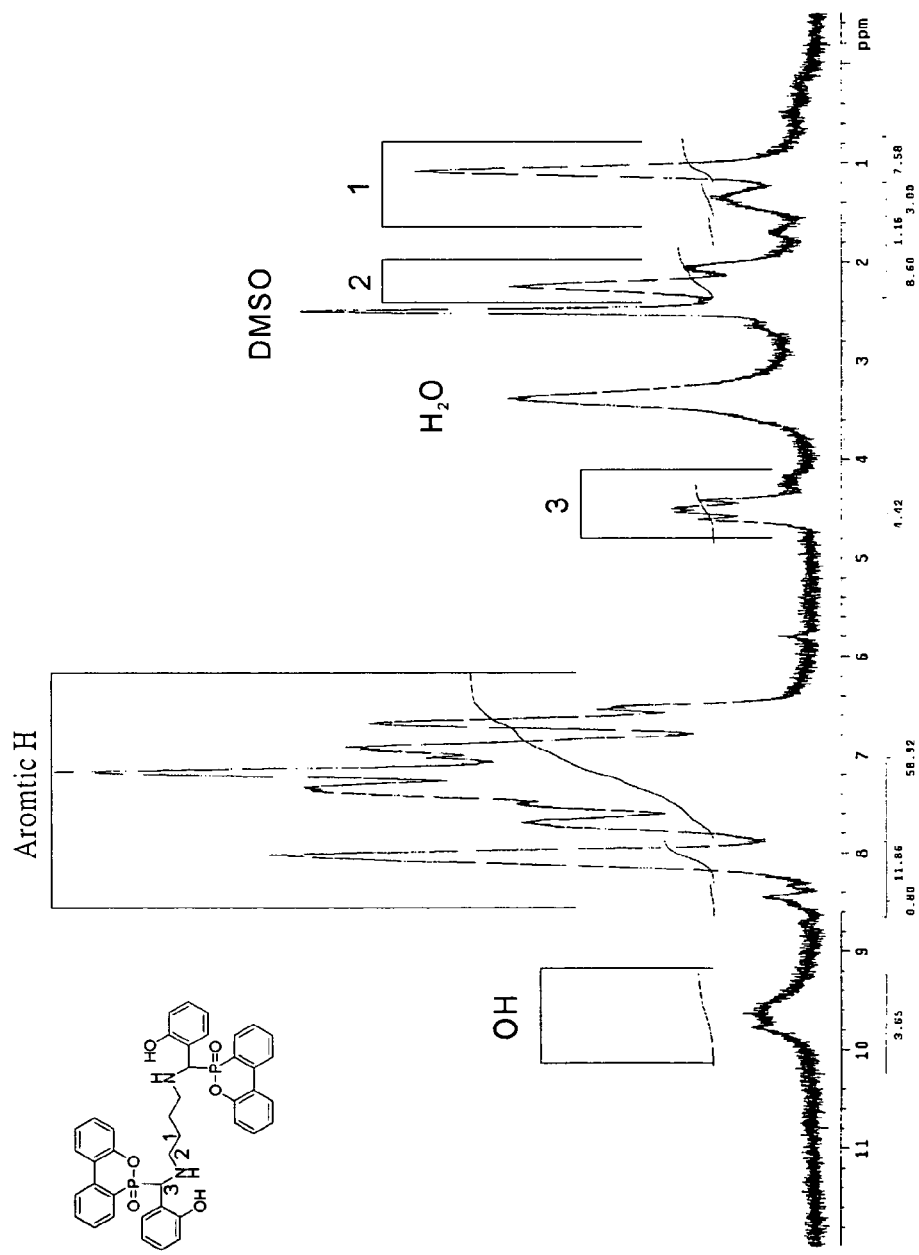
FIG. 4B is 1H-NMR spectrum of the intermediate compound P—$C_4$—HB according to the example 6 of this invention.

Stage (II) Synthesis of the monomer P—C$_4$—HB. After dissolving 5 g (16.88 mmol) of C$_4$—HB to 30 ml ethanol within a 100 ml three-neck flask, 7.302 g (16.88×2 mmol) of DOPO is added to the three-neck flask. The mixture is stirred at room temperature for 12 hours with precipitates. The mixture is poured into de-ionized water for yellow precipitates. After filtration, vacuum evaporation and baking, 11.8963 g of light yellow powder P—C$_4$—HB is obtained with a yield rate of 96.8%. The results are shown in FIG. 4B. FIG. 4B is 1H-NMR spectrum of the intermediate product P—C$_4$—HB. The structure of the synthesized P—C$_4$—HB can be verified by the figure.

Figure 4C:
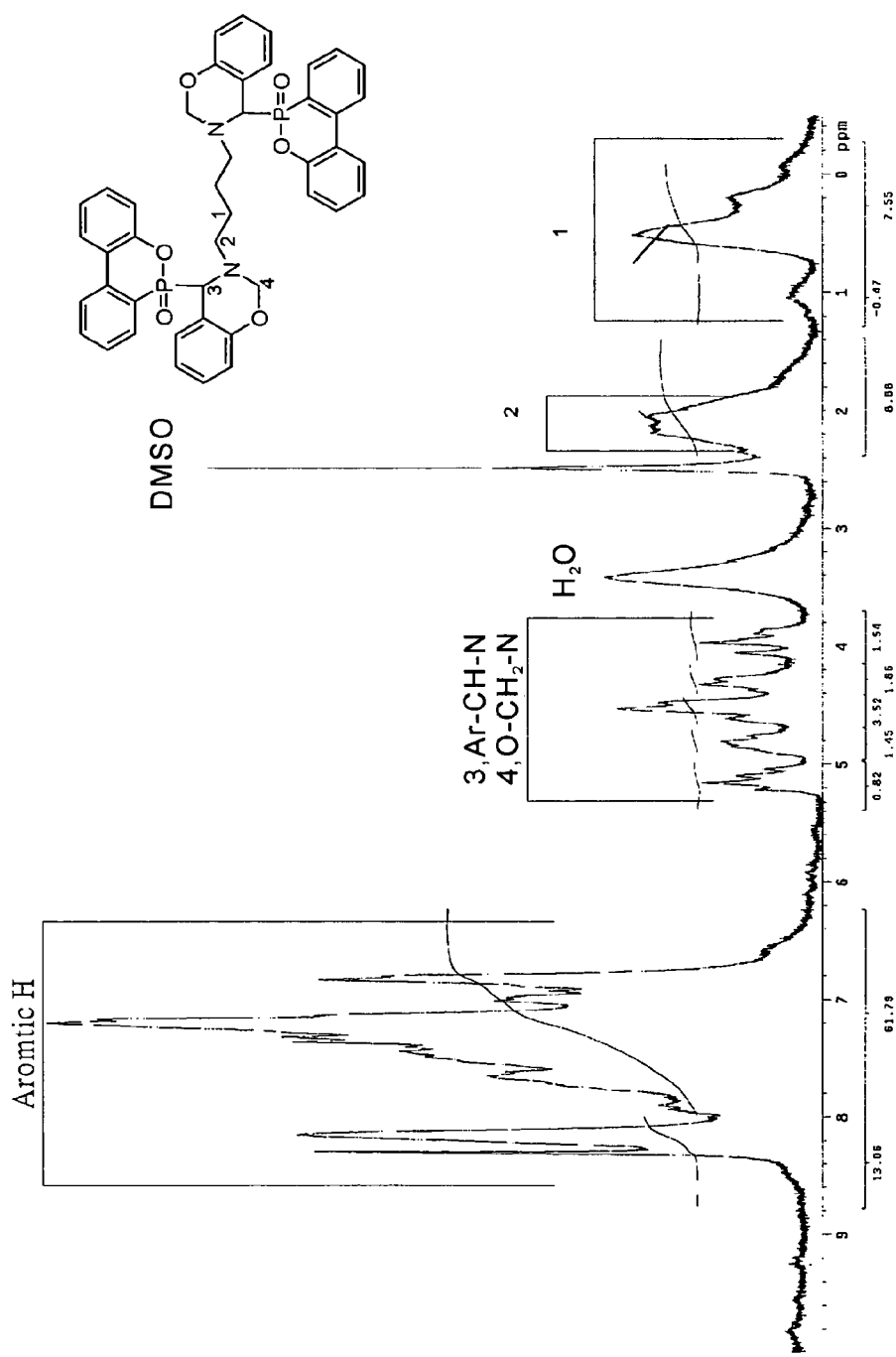
FIG. 4C is 1H-NMR spectrum of the compound P—$C_4$-Bz according to the example 6 of this invention.

Stage (III) Synthesis of the monomer P—C$_4$-Bz. After dissolving 5 g (13.7 mmol) of P—C$_4$—HB to 100 ml chloroform within a 500 ml three-neck flask, 1.11 g (13.7×2 mmol) of formaldehyde solution (37%) is added drop-wise to the three-neck flask. The mixture is stirred at room temperature (35° C.) for 1 hour, heated to the reflux temperature and keep stirring for 10 hours, and then vacuum evaporated to obtain yellow-whitish powder P—C$_4$-Bz. The results are shown in FIG. 4C. FIG. 4C is 1H-NMR spectrum of the product P—C$_4$-Bz. The structure of the synthesized P—C$_4$-Bz can be verified by the figure.

EXAMPLE 7
Three-Stage Synthesis of the Compound P—C$_6$—Bz
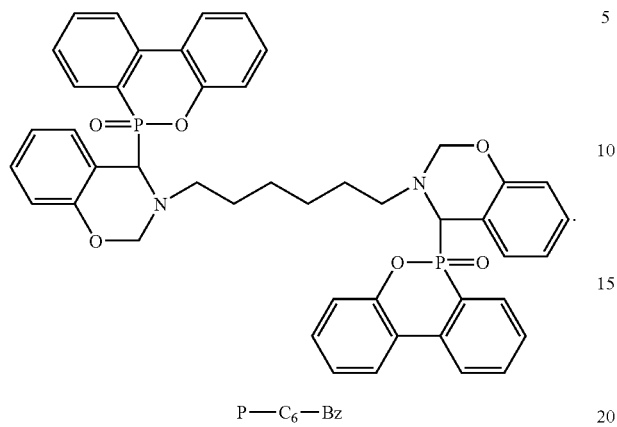
P—C$_6$—Bz
Three-stage synthesis of P—C$_6$—B: Stage (I) Synthesis of the intermediate product C$_6$—HB; Stage (II) Synthesis of the intermediate product P—C$_6$—HB; Stage (III) Synthesis of the monomer P—C$_6$—Bz. The reaction is as follows:
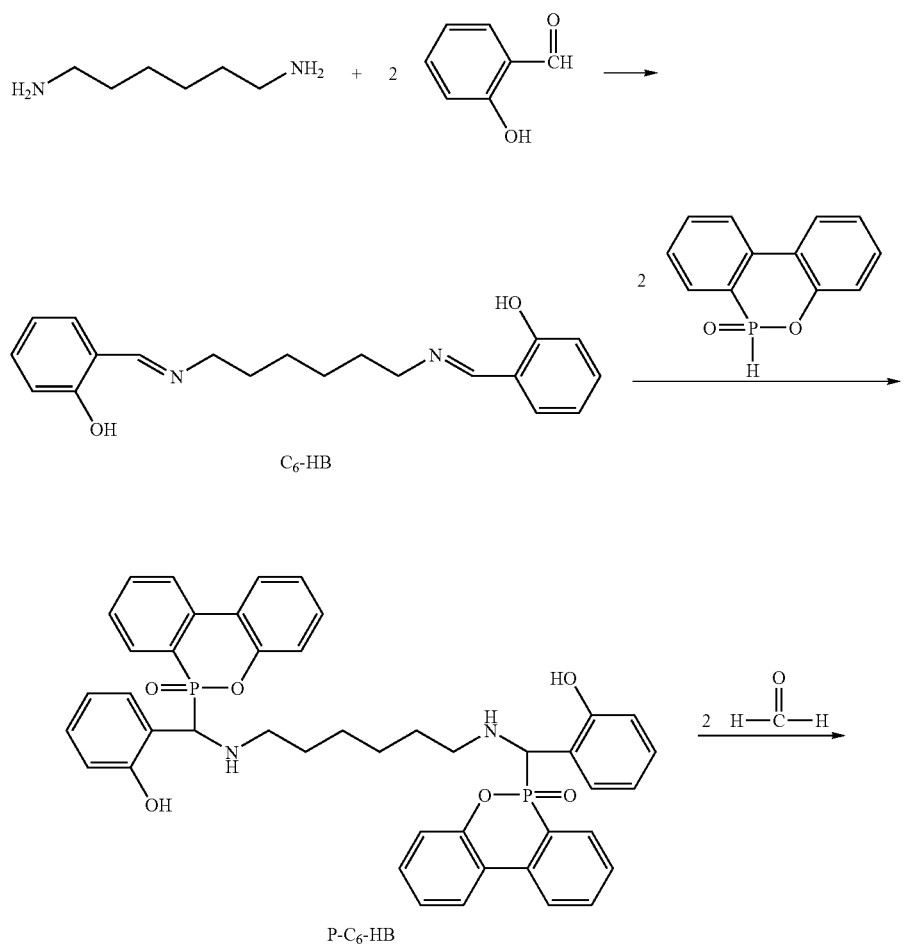

-continued

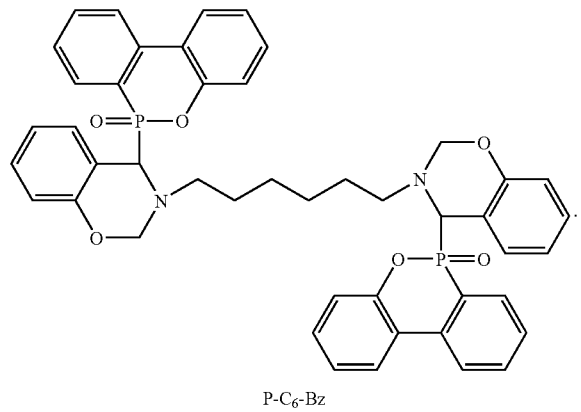

P-C₆-Bz

Figure 5A:
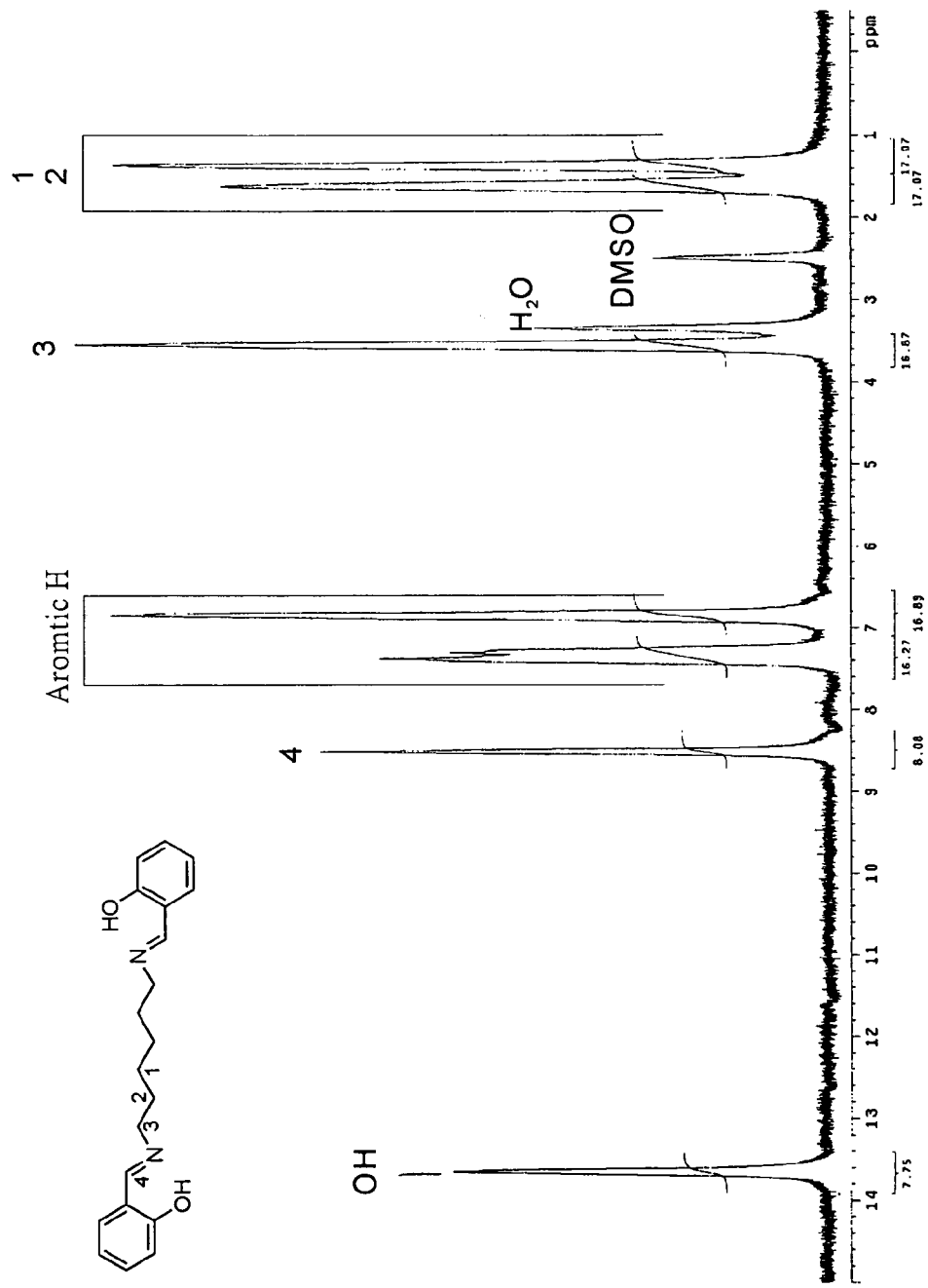
FIG. 5A is 1H-NMR spectrum of the intermediate compound $C_6$—HB according to the example 7 of this invention.

Stage (I) Synthesis of the intermediate product C₆—HB. 2-HB 20.32 g (2×83.25 mmol) and 1,6-hexanediamine 5 g (83.25 mmol) are dissolved in 50 ml DMF within a three-neck flask and stirred under nitrogen with yellow precipitates and slightly exothermic. Under room temperature, the mixture keeps stirring for 6 hours and is then poured into de-ionized water for precipitates. After filtration, vacuum evaporation and vacuum oven at 100° C., 13.5465 g yellow powder C₆—HB is obtained with a yield rate of 97%. Melting point 74.33° C. The results are shown in FIG. 5A. FIG. 5A is 1H-NMR spectrum of the intermediate product C₆—HB. The structure of the synthesized C₆—HB can be verified by the figure.

Figure 5B:
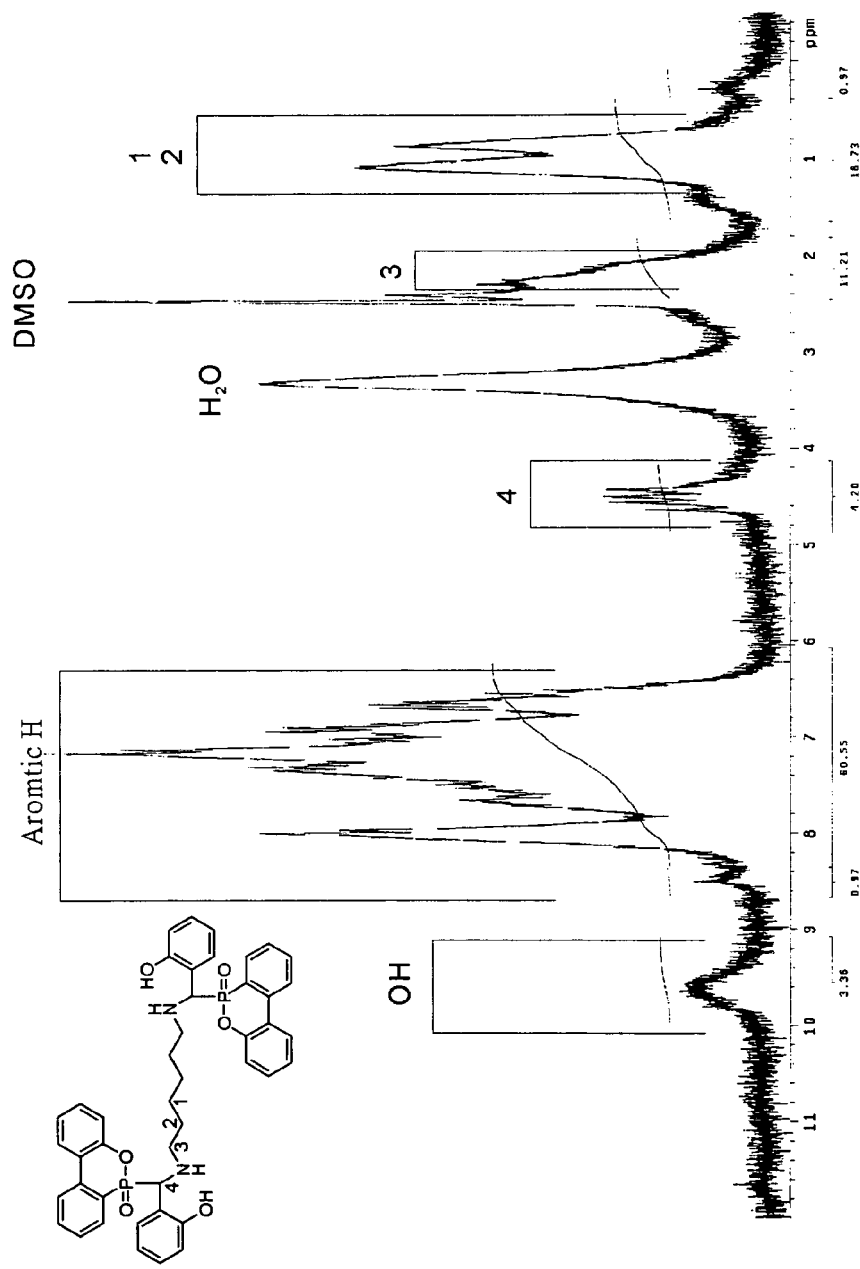
FIG. 5B is 1H-NMR spectrum of the intermediate compound P—$C_6$—HB according to the example 7 of this invention.

Stage (II) Synthesis of the monomer P—C₆—HB. After dissolving 5 g (15.42 mmol) of C₆—HB to 30 ml ethanol within a 100 ml three-neck flask, 6.662 g (15.42×2 mmol) of DOPO is added to the three-neck flask and stirred under room temperature for 12 hours with precipitates. The mixture is poured into de-ionized water for precipitates. After filtration, vacuum evaporation and baking, 11.8963 g light yellow powder P—C₆—HB is obtained with a yield rate of 96.8%. The results are shown in FIG. 5B. FIG. 5B is 1H-NMR spectrum of the intermediate product P—C₆—HB. The structure of the synthesized P—C₆—HB can be verified by the figure.

Figure 5C:
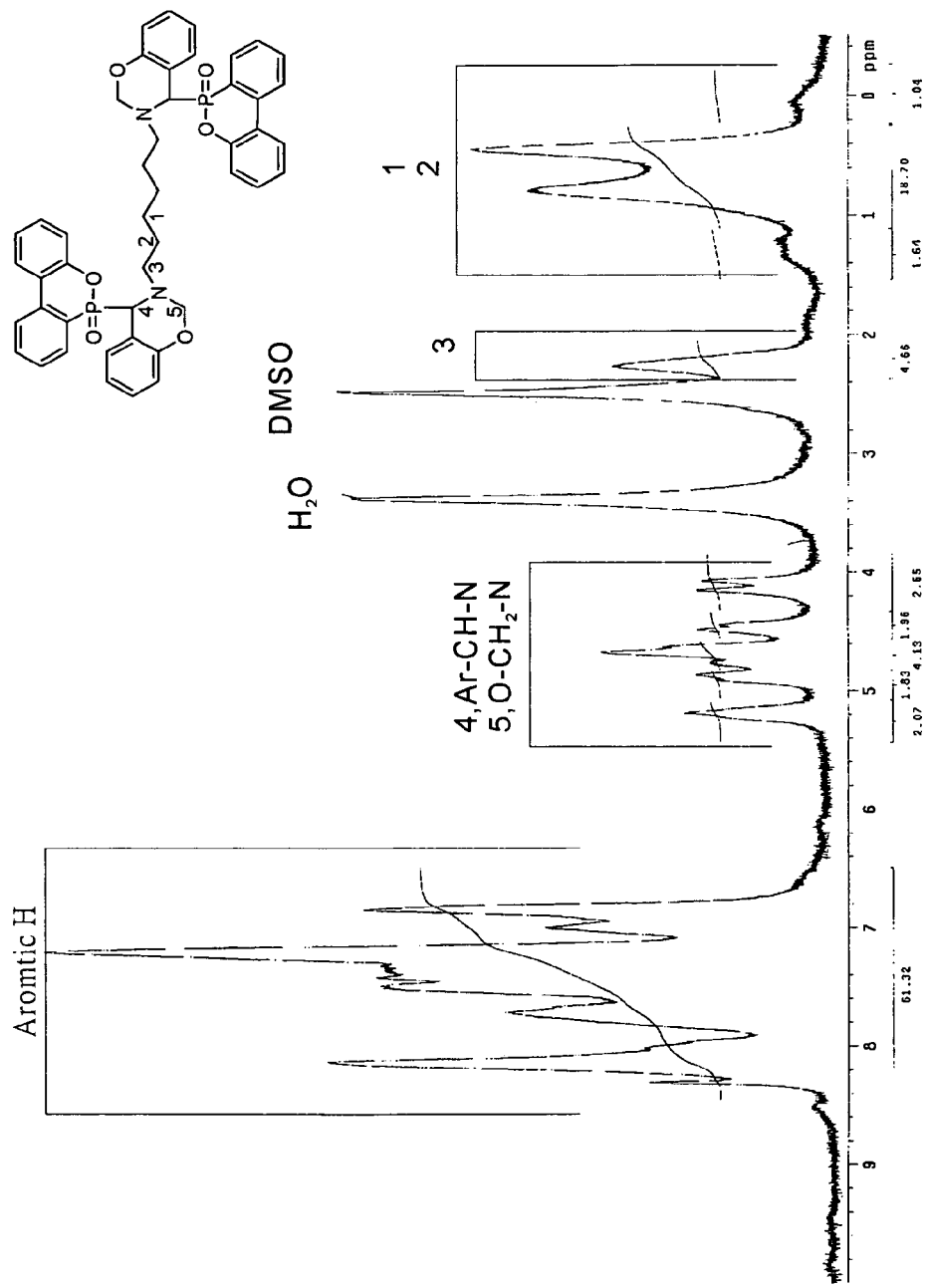
FIG. 5C is 1H-NMR spectrum of the compound P—$C_6$-Bz according to the example 7 of this invention.

Stage (III) Synthesis of the monomer P—C₆—Bz. After dissolving 5 g (13.2 mmol) of P—C₆—HB to 100 ml chloroform within a 500 ml three-neck flask, 1.11 g (13.2×2 mmol) of formaldehyde solution (37%) is added drop-wise to the three-neck flask. The mixture is stirred at room temperature (35° C.) for 1 hour, heated to the reflux temperature and keep stirring for 10 hours, and then vacuum evaporated to obtain yellow-whitish powder P—C₆—Bz. The results are shown in FIG. 5C. FIG. 5C is 1H-NMR spectrum of the product P—C₆—Bz. The structure of the synthesized P—C₆—Bz can be verified by the figure.

EXAMPLE 8

Three-stage synthesis of the following compound P—C₈-Bz

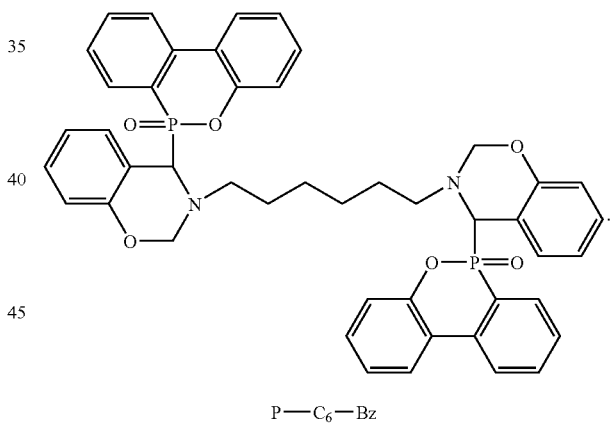

P—C₆—Bz

Three-stage synthesis of P—C₈-Bz: Stage (I) Synthesis of the intermediate product C₈—HB; Stage (II) Synthesis of the intermediate product P—C₈—HB; Stage (III) Synthesis of the monomer P—C₈-Bz. The reaction is as follows:

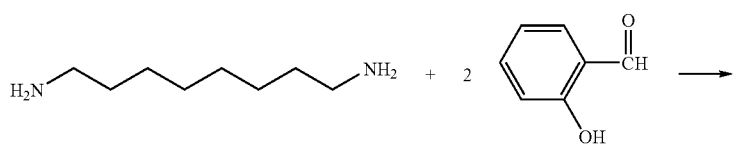

-continued

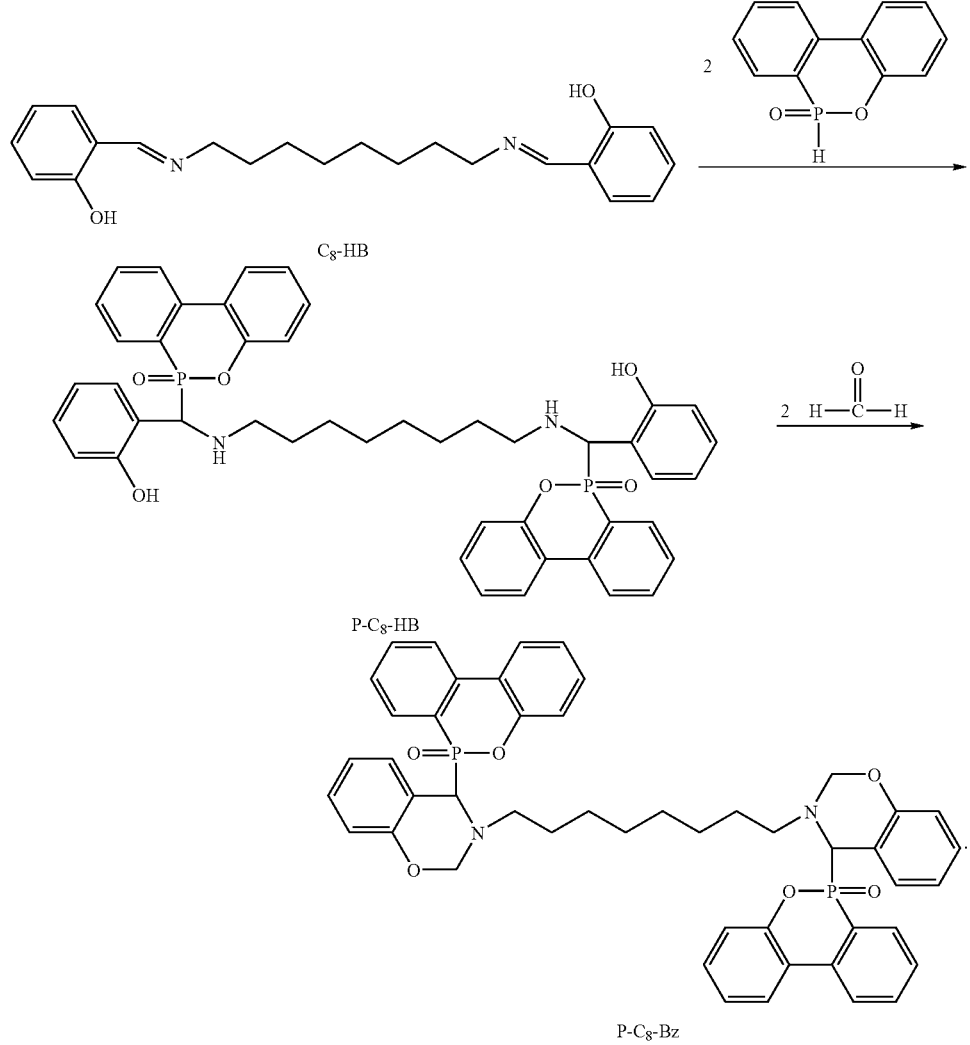

Figure 6A:
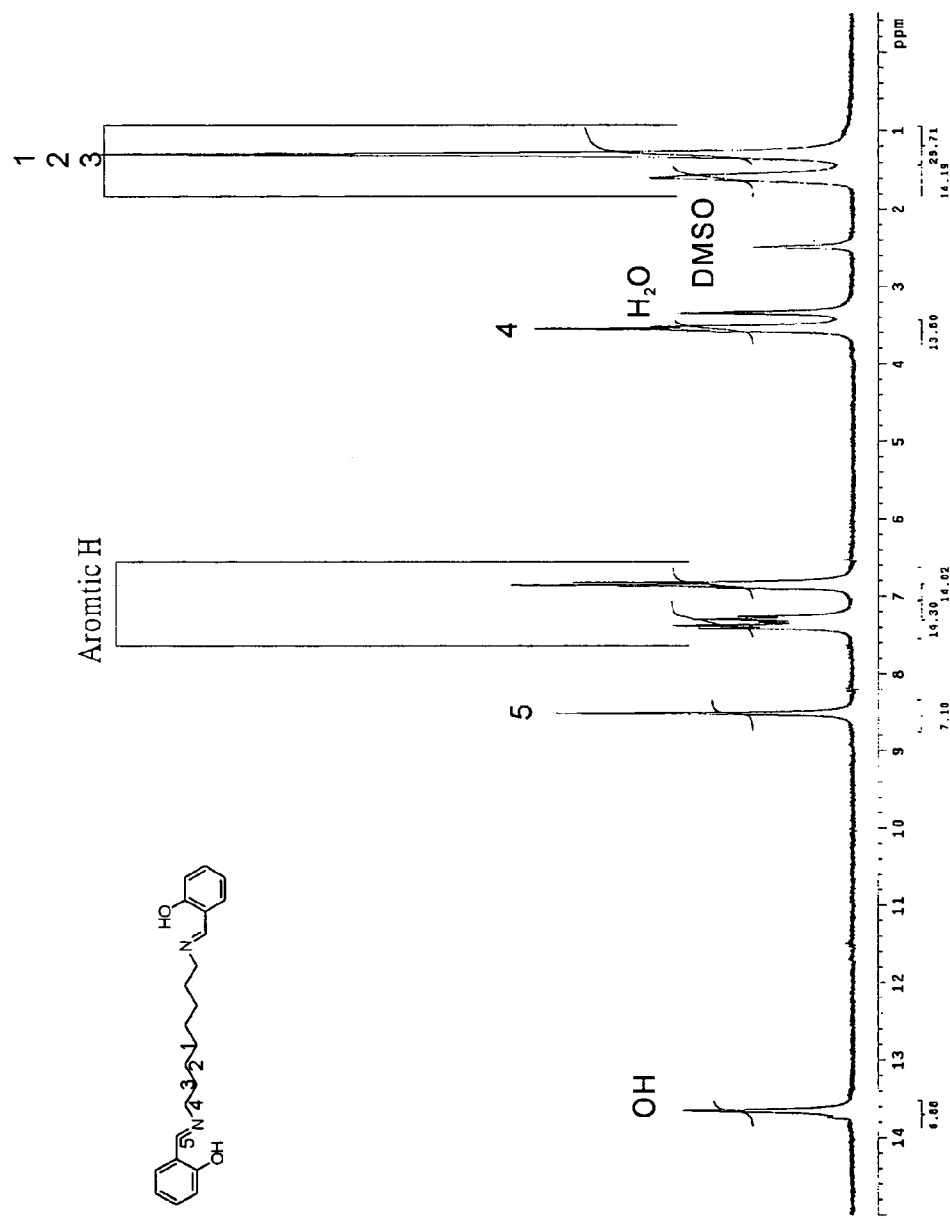
FIG. 6A is 1H-NMR spectrum of the intermediate compound $C_8$—HB according to the example 8 of this invention.

Stage (I) Synthesis of the intermediate product $C_8$—HB. 2-HB 20.32 g (2×83.25 mmol) and 1,8-octanediamine 5 g (83.25 mmol) are dissolved in 50 ml DMF within a three-neck flask and stirred under nitrogen with yellow precipitates and slightly exothermic. Under room temperature, the mixture is stirring for 6 hours and then poured into de-ionized water for precipitates. After filtration, vacuum evaporation and vacuum oven at 100° C., 11.8216 g yellow powder $C_8$—HB is obtained with a yield rate of 96.7%. Melting point 76.83° C. The results are shown in FIG. 6A. FIG. 6A is 1H-NMR spectrum of the intermediate product $C_8$—HB. The structure of the synthesized $C_8$—HB can be verified by the figure.

Figure 6B:
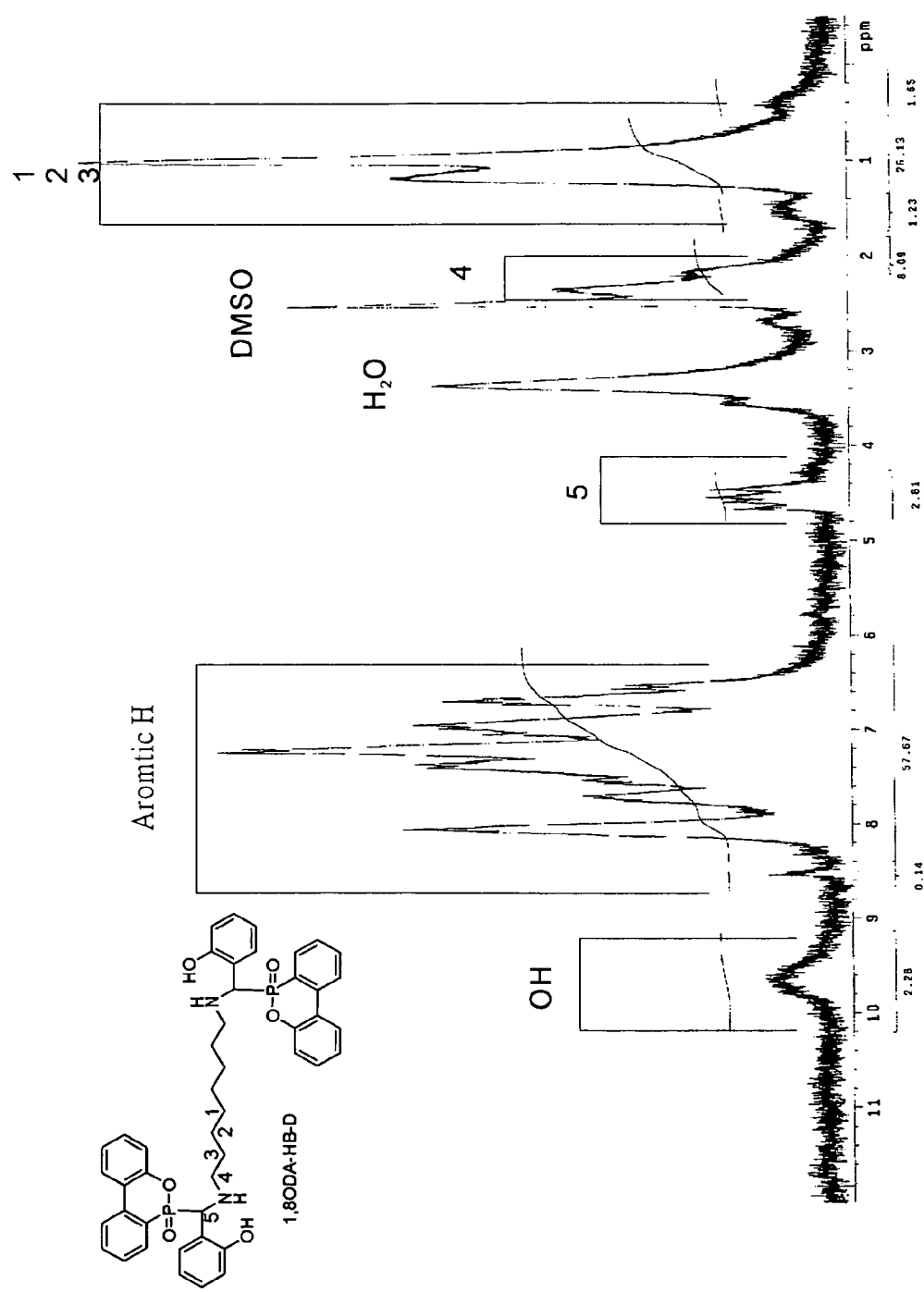
FIG. 6B is 1H-NMR spectrum of the intermediate compound P—$C_8$—HB according to the example 8 of this invention.

Stage (II) Synthesis of the monomer P—$C_8$—HB. After dissolving 5 g (14.2 mmol) of $C_8$—HB to 30 ml ethanol within a 100 ml three-neck flask, DOPO 6.1353 g (14.2×2 mmol) is added to the three-neck flask. The mixture is stirred under room temperature for 12 hours with yellow precipitates. The mixture is poured into de-ionized water for yellow precipitates. After filtration, vacuum evaporation and baking, 10.4892 g light yellow powder P—$C_8$—HB is obtained with a yield rate of 94.2%. The results are shown in FIG. 6B. FIG. 6B is 1H-NMR spectrum of the intermediate product P—$C_8$—HB. The structure of the synthesized P—$C_8$—HB can be verified by the figure.

Figure 6C:
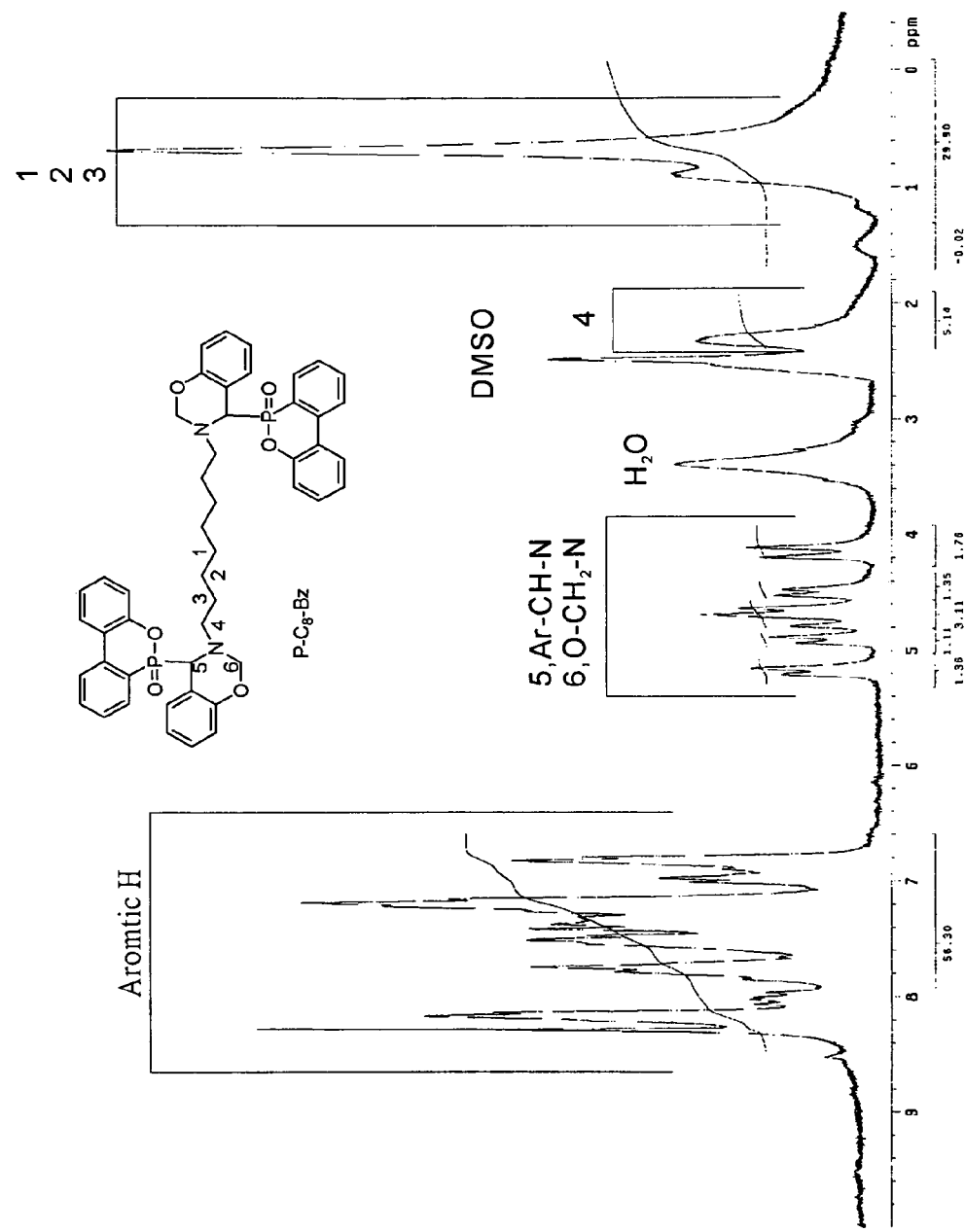
FIG. 6C is 1H-NMR spectrum of the compound P—$C_8$-Bz according to the example 8 of this invention.

Afterwards, Stage (III) Synthesis of the monomer P—$C_8$-Bz. After dissolving 5 g (12.7 mmol) of P—$C_8$—HB to 100 ml chloroform within a 500 ml three-neck flask, 1.03 g (12.7×2 mmol) of formaldehyde solution (37%) is added drop-wise to the three-neck flask. The mixture is stirred at room temperature (35° C.) for 1 hour, heated to the reflux temperature and keep stirring for 10 hours, and then vacuum evaporated to obtain yellow-whitish powder P—$C_8$-Bz. The results are shown in FIG. 6C. FIG. 6C is 1H-NMR spectrum of the product P—$C_8$-Bz. The structure of the synthesized P—$C_8$-Bz can be verified by the figure.

The above embodiments uses several amines with different electron-pushing or -pulling groups to synthesize benzoxazine. For example, DDS has strong electron-pulling group —$SO_2$—, BAPP has strong electron-pushing group —O—, while aliphatic diamine DDM has weak electron-pushing group —$CH_2$—. However, the above examples merely try to explain the principles of this invention by exemplifying the reaction mechanisms of the amines of various electron pushing or pulling capabilities, but not to limit the scope of this invention. The present invention may also employ other amines such as aromatic amines (di-amines, tri-amines or tetra-amines) or aliphatic amines to prepare the phosphorus-based oxazine compounds with various structures through analogous reactions.

The preparation method of the present invention may employ bi-functional group or poly-functional group amines or aliphatic di-amines to synthesize phosphorus-based oxazine compounds of high purity and of a high yield rate.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A phosphorus-based oxazine compound with a structure as shown in formula (I):

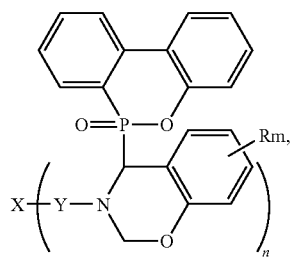

formula (I)

wherein n represents 2, X represents a single bond or

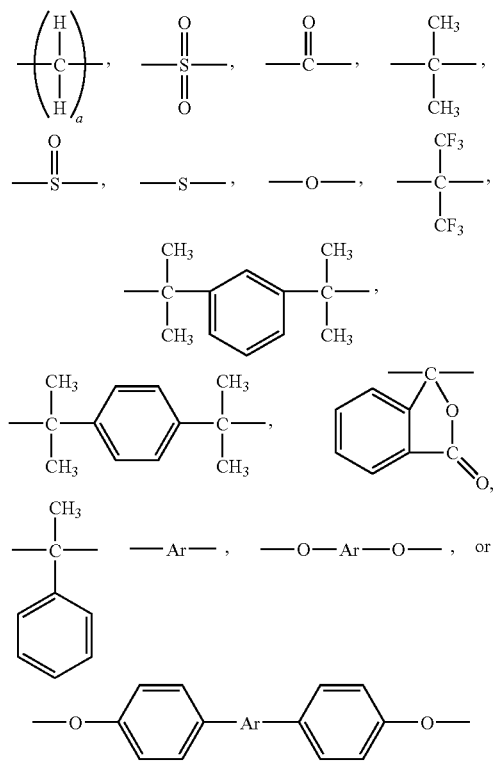

wherein a is an integer ranging from 1 to 16, Ar represents

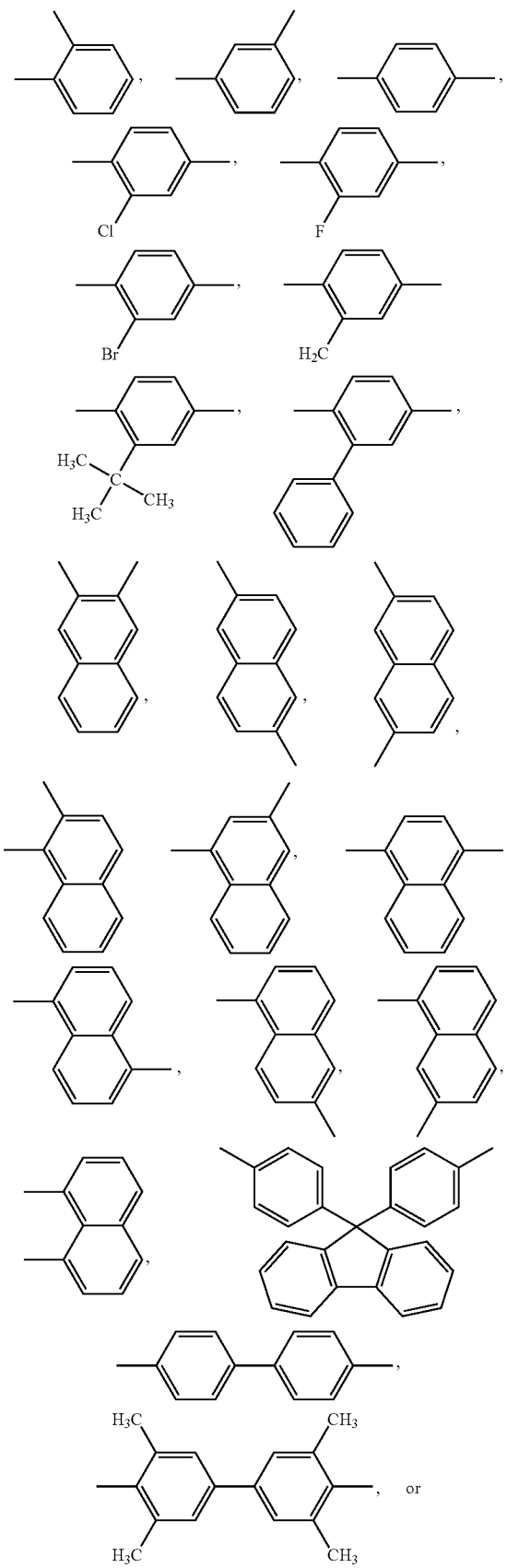

-continued

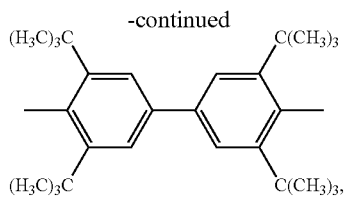

Y represents

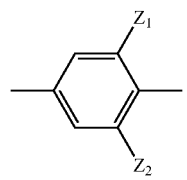

or a single bond, wherein $Z_1$ or $Z_2$ individually represents a hydrogen, a $C_1$-$C_6$ alkyl group, a $C_1$-$C_6$ alkoxyl group, $CF_3$, a phenyl group, a halogen group, a phenoxy group or a $C_3$-$C_7$ cyclic alkyl group, m represents 1 or 2, R represents a hydrogen, a $C_1$-$C_6$ alkyl group, a $C_1$-$C_6$ alkoxyl group, $CF_3$, $OCF_3$, a phenyl group, a halogen group, a phenoxy group or a $C_3$-$C_7$ cyclic alkyl group, and when m is 2, R represents the same or different groups.

2. The compound of claim 1, wherein X is a center of symmetry.

3. A preparation method of a phosphorus-based oxazine compound, wherein the phosphorus-based oxazine compound has a structure as shown in formula (II):

formula (II)

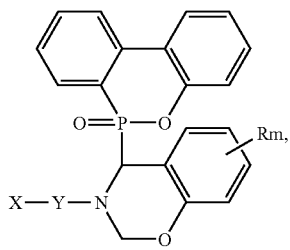

wherein X represents a hydrogen, a $C_1$-$C_6$ alkyl group, a $C_1$-$C_6$ alkoxyl group, $CF_3$, $OCF_3$, a phenyl group, a halogen group, a phenoxy group or a $C_3$-$C_7$ cyclic alkyl group, Y represents

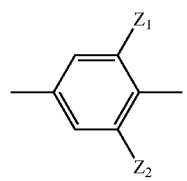

or a single bond, wherein $Z_1$ or $Z_2$ individually represents a hydrogen, a $C_1$-$C_6$ alkyl group, a $C_1$-$C_6$ alkoxyl group, $CF_3$, a phenyl group, a halogen group, a phenoxy group or a $C_3$-$C_7$ cyclic alkyl group, m represents 1 or 2, R represents a hydrogen, a $C_1$-$C_6$ alkyl group, a $C_1$-$C_6$ alkoxyl group, $CF_3$, $OCF_3$, a phenyl group, a halogen group, a phenoxy group or a $C_3$-$C_7$ cyclic alkyl group, and when m is 2, R represents the same or different groups, wherein the preparation method of the phosphorus-based oxazine compound comprises:

mixing the following compounds

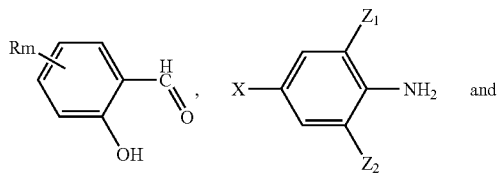

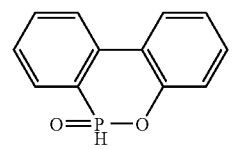

to form a compound of the following formula (III):

formula (III)

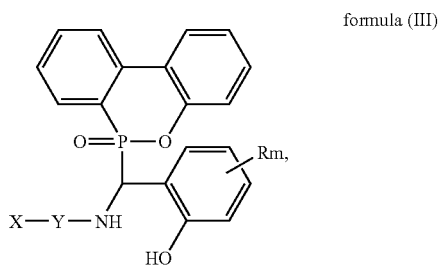

wherein X, Y, R and m are defined as described in the above formula (II); and adding formaldehyde or trioxymethylene to obtain the phosphorus-based oxazine compound.

4. The preparation method of claim 3, wherein the compound of formula (III) is formed in a single step by simultaneously contacting and mixing the following compounds

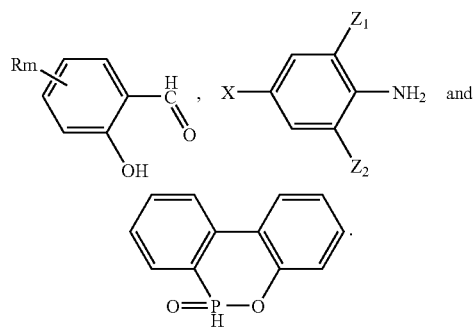

5. The preparation method of claim 3, wherein the compound of formula (III) is formed in two-stage by first contacting and mixing

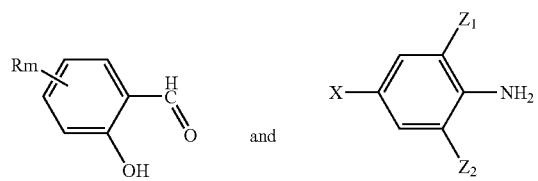

to form a compound of the following formula (IV),

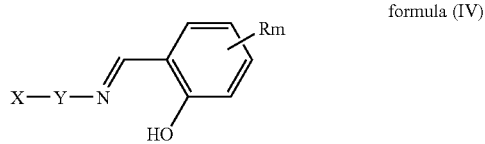

formula (IV)

and followed by adding the compound

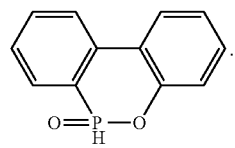

6. A preparation method of a phosphorus-based oxazine compound,. wherein the phosphorus-based oxazine compound has a structure as shown in formula (V):

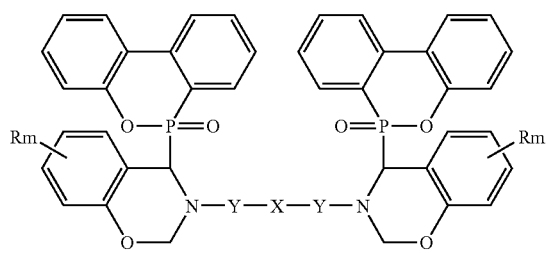

formula (V)

wherein X represents a single bond or

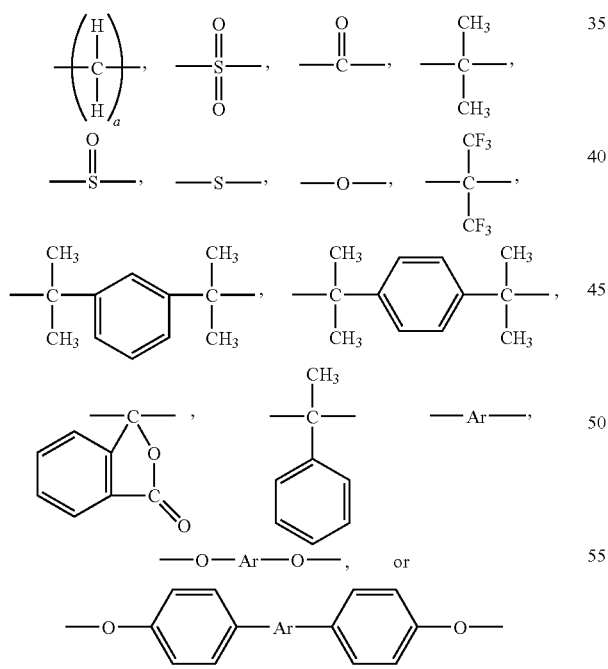

—O—Ar—O—, or

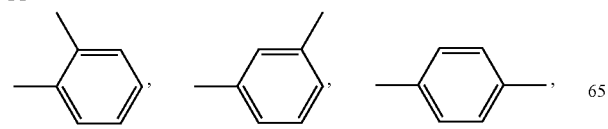

wherein a is an integer ranging from 1 to 16, Ar represents application Ser. No. 12/017,067

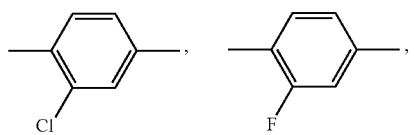

-continued

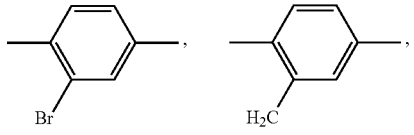

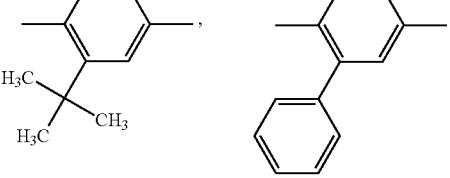

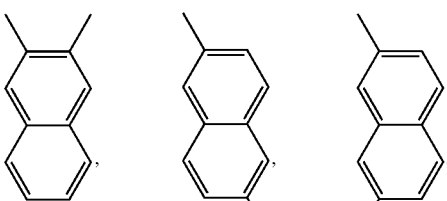

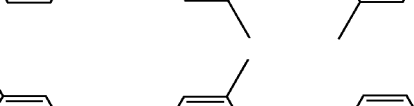

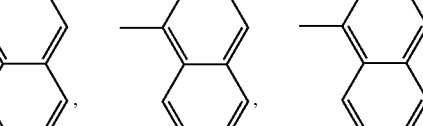

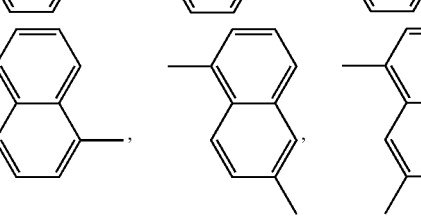

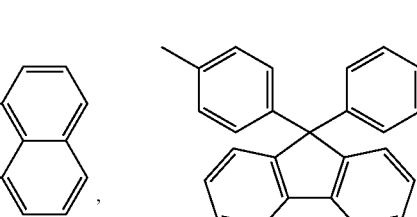

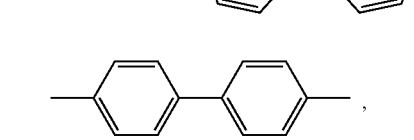

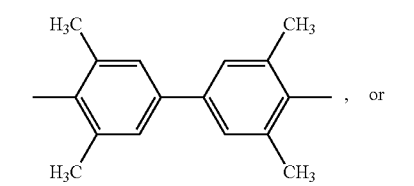

-continued

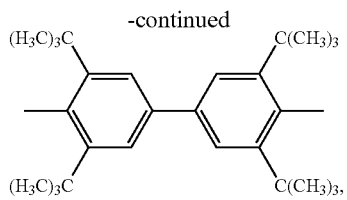

Y represents

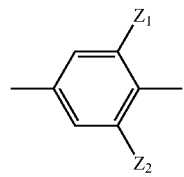

or a single bond, wherein $Z_1$ or $Z_2$ individually represents a hydrogen, a $C_1$-$C_6$ alkyl group, a $C_1$-$C_6$ alkoxyl group, $CF_3$, a phenyl group, a halogen group, a phenoxy group or a $C_3$-$C_7$ cyclic alkyl group, m represents 1 or 2, R represents a hydrogen, a $C_1$-$C_6$ alkyl group, a $C_1$-$C_6$ alkoxyl group, $CF_3$, $OCF_3$, a phenyl group, a halogen group, a phenoxy group or a $C_3$-$C_7$ cyclic alkyl group, and when m is 2, R represents the same or different groups, wherein the preparation method of the phosphorus-based oxazine compound comprises:

mixing the following compounds

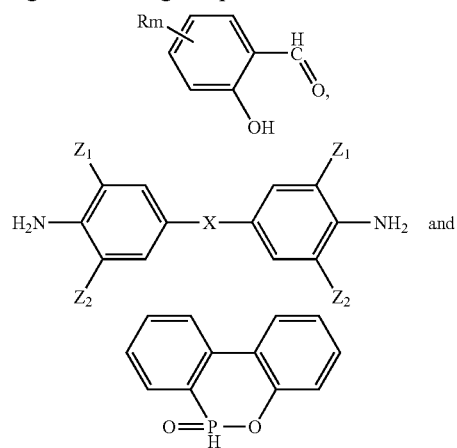

to form a compound of the following formula (VI):

formula (II)

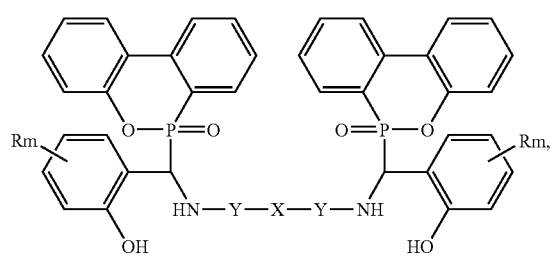

wherein X, Y, R and m are defined as described in the above formula (V); and adding formaldehyde or trioxymethylene to obtain the phosphorus-based oxazine compound.

7. The preparation method of claim 6, wherein the compound of formula (VI) is formed in a single step by simultaneously contacting and mixing the following compounds

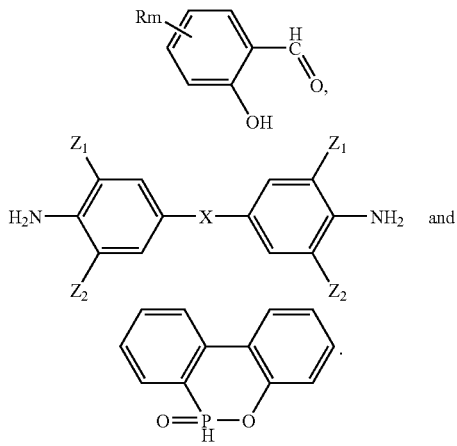

8. The preparation method of claim 6, wherein the compound of formula (VI) is formed in two-stage by first contacting and mixing the following compounds

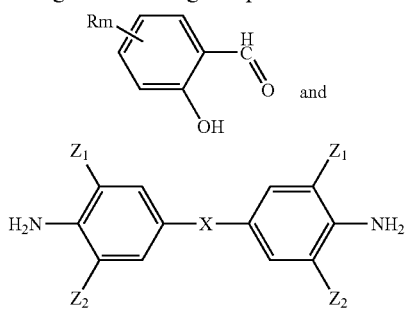

to form a compound of the following formula (VII):

formula (VII)

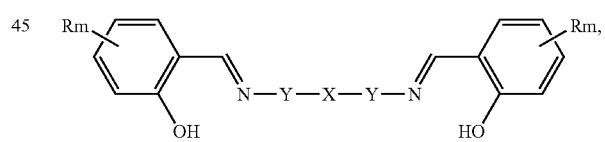

wherein X, Y, R and m are defined as described in the above formula (V), and followed by adding the compound

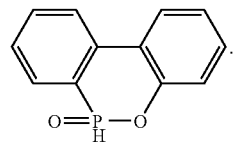

* * * * *